(12) United States Patent
Bar-Sagi et al.

(10) Patent No.: US 12,016,881 B2
(45) Date of Patent: Jun. 25, 2024

(54) METHODS AND REAGENTS FOR MODULATING MACROPHAGE PHENOTYPE

(71) Applicant: NEW YORK UNIVERSITY, New York, NY (US)

(72) Inventors: Dafna Bar-Sagi, New York, NY (US); Jane Cullis, New York, NY (US); Craig Ramirez, Short Hills, NJ (US)

(73) Assignee: NEW YORK UNIVERSITY, New York, NY (US)

( * ) Notice: Subject to any disclaimer, the term of this patent is extended or adjusted under 35 U.S.C. 154(b) by 229 days.

(21) Appl. No.: 17/396,792

(22) Filed: Aug. 9, 2021

(65) Prior Publication Data
US 2022/0031741 A1 Feb. 3, 2022

Related U.S. Application Data

(62) Division of application No. 16/306,636, filed as application No. PCT/US2017/035959 on Jun. 5, 2017, now Pat. No. 11,110,122.

(60) Provisional application No. 62/345,591, filed on Jun. 3, 2016.

(51) Int. Cl.
| | |
|---|---|
| *A61K 38/38* | (2006.01) |
| *A61K 31/337* | (2006.01) |
| *A61K 35/15* | (2015.01) |
| *A61K 38/00* | (2006.01) |
| *A61K 38/18* | (2006.01) |
| *A61K 38/19* | (2006.01) |
| *A61K 38/20* | (2006.01) |
| *A61P 35/00* | (2006.01) |
| *C07K 14/52* | (2006.01) |
| *C07K 14/53* | (2006.01) |
| *C07K 14/54* | (2006.01) |
| *C07K 14/76* | (2006.01) |
| *C07K 14/765* | (2006.01) |
| *C12N 5/0786* | (2010.01) |

(52) U.S. Cl.
CPC ............ *A61K 35/15* (2013.01); *A61K 31/337* (2013.01); *A61K 38/00* (2013.01); *A61K 38/18* (2013.01); *A61K 38/19* (2013.01); *A61K 38/193* (2013.01); *A61K 38/20* (2013.01); *A61K 38/2006* (2013.01); *A61K 38/2026* (2013.01); *A61K 38/2066* (2013.01); *A61K 38/385* (2013.01); *A61P 35/00* (2018.01); *C07K 14/52* (2013.01); *C07K 14/53* (2013.01); *C07K 14/54* (2013.01); *C07K 14/5406* (2013.01); *C07K 14/5428* (2013.01); *C07K 14/76* (2013.01); *C07K 14/765* (2013.01); *C12N 5/0645* (2013.01); *C12N 2501/22* (2013.01); *C12N 2501/2301* (2013.01); *C12N 2501/2304* (2013.01); *C12N 2501/2306* (2013.01); *C12N 2501/231* (2013.01); *C12N 2501/2333* (2013.01); *C12N 2501/24* (2013.01); *C12N 2501/25* (2013.01)

(58) Field of Classification Search
CPC .. A61K 38/1774; A61K 38/38; A61K 38/385; A61K 38/177; A61K 35/15; A61K 31/337; C07K 14/70503; C07K 14/70535; C07K 17/02; C07K 17/00; C07K 14/76; C07K 14/765
See application file for complete search history.

(56) References Cited

U.S. PATENT DOCUMENTS

| | | | |
|---|---|---|---|
| 8,314,156 B2 | 11/2012 | Desai et al. | |
| 8,822,417 B2 | 9/2014 | Anderson et al. | |
| 2005/0014934 A1* | 1/2005 | Hinton | C07K 16/249 530/387.3 |
| 2007/0135620 A1* | 6/2007 | Chamberlain | C07K 16/32 530/387.3 |
| 2009/0041770 A1* | 2/2009 | Chamberlain | C07K 16/082 424/134.1 |
| 2009/0163699 A1* | 6/2009 | Chamberlain | C07K 16/4291 530/387.3 |
| 2012/0122207 A1 | 5/2012 | Sieweke | |
| 2012/0220530 A1* | 8/2012 | Plumridge | C07K 14/765 536/23.4 |
| 2012/0322739 A1* | 12/2012 | Andersen | A61P 7/00 977/773 |
| 2013/0028930 A1 | 1/2013 | Plumridge et al. | |
| 2013/0225496 A1 | 8/2013 | Plumridge et al. | |
| 2014/0128326 A1* | 5/2014 | Cameron | A61K 39/385 435/69.6 |
| 2015/0086603 A1 | 3/2015 | Hossainy et al. | |

(Continued)

OTHER PUBLICATIONS

Andersen et al. FcRn binding properties of an abnormal truncated analbuminemic albumin variant. Clin Biochem 43: 367-372, 2010.*

(Continued)

*Primary Examiner* — Bridget E Bunner
(74) *Attorney, Agent, or Firm* — Troutman Pepper Hamilton Sanders LLP (Rochester)

(57) ABSTRACT

The present invention is directed to methods of inducing a phenotypic change in a population of monocytes and/or macrophages. The method includes administering to the population of monocytes and/or macrophages, a macrophage stimulating agent coupled to a carrier molecule, wherein the carrier molecule facilitates macropinocytic uptake of the agent by monocytes and macrophages in the population and is defective in neonatal Fc receptor binding, wherein the administering induces a phenotypic change in the monocytes and macrophages in the population.

19 Claims, 11 Drawing Sheets
Specification includes a Sequence Listing.

(56) References Cited

U.S. PATENT DOCUMENTS

2016/0075763 A1  3/2016  Sleep et al.

OTHER PUBLICATIONS

Hao et al. Macrophages in Tumor Microenvironments and the Progression of Tumors. Clin Dev Immunol vol. 2012: 948098, 2012 (11 total pages).*
Hornok, V. Serum Albumin Nanoparticles: Problems and Prospects. Polymers 13: 3759, 2021 (12 total pages).*
Iwao et al. Changes of net charge and alpha-helical content affect the pharmacokinietic properties of human serum albumin. Biochem Biophys Acta 1774: 1582-1590, 2007.*
Kim et al. Tumor-Associated Macrophages and Neutrophils in Tumor Microenvironment. Med Inflamm Volumn 2016: 6058147, 2016 (11 total pages).*
Kuo et al. Neonatal Fc Receptor: From Immunity to Therapeutics. J Clin Immunol 30: 777-789, 2010.*
Pan et al. Tumor-Associated Macrophages in Tumor Immunity. Front Immunol 11: 583084, 2020.*
Sand et al. Unraveling the interaction between FcRn and albumin: opportunities for design of albumin-based therapeutics. Front Immunol 5: 682, 2015.*
Sleep, D. Albumin and its application in drug delivery. Exp Opin Drug Delivery 12(5): 793-812, 2014.*
Takeya et al. Role of tumor-associated macrophages in human malignancies: friend or foe? Pathol Int 66: 491-505, 2016.*
Zhu et al. MHC Class I-Related Neonatal Fc Receptor for IgG Is Functionally Expressed in Monocytes, Intestinal Macrophages, and Dendritic Cells. J Immunol 166(5): 3266-3276, 2001.*
International Search Report and Written Opinion for corresponding Application No. PCT/US2017/035959 (dated Oct. 31, 2017).
Sockolosky et al., "The Neonatal Fc Receptor, FcRn, as a Target for Drug Delivery and Therapy," Adv. Drug Deliv. Rev. 91:1-40 (2015).
Andersen et al., "Structure-based Mutagenesis Reveals the Albumin-binding site of neonatal Fc Receptor," Nat. Comm. 3:610 (2012).
Tanei et al., "Redirecting Transport of Nanoparticle Albumin-Bound Paclitaxel to Macrophages Enhances Therapeutic Efficacy against Liver Metastases," Cancer Research 76(2): 429-39 (2016).
Cullis et al., "Nab-paclitaxel and Agonist CD40 mAb Combination Therapy Induces Tumor-associated Macrophage Polarization Switching in Pancreatic Cancer," (abstract) Abstract No. LB-224 for Poster Presentation at AACR Annual Meeting, Apr. 21, 2015.
Ha et al., "Macropinocytosis Exploitation by Cancers and Cancer Therapeutics," Front Physiol 7:381 (2016).
Hume et al., "Macrophages Exposed Continuously to Lipopolysaccharide and Other Agonists That Act Via Toll-like Receptors Exhibit a Sustained and Additive Activation State," BMC Immunol 2:11 (2001).
Jones et al., "Different Toll-like Receptor Agonists Induce Distinct Macrophage Responses," J Leukocyte Biol 69:1036-1044 (2001).
Kenanova et al., "HSA Domain III as a Protein Scaffold With Defined Serum Pharmacokinetics," J Nucl Med 50 (Suppl 2):1582 (2009).
Kratz et al., "Albumin as a Drug Carrier: Design of Prodrugs, Drug Conjugates and Nanoparticles," J Control Release 132:171-183 (2008).
Cullis et al., "Macropinocytosis of Nab-paclitaxel Drives Macrophage Activation in Pancreatic Cancer," Cancer Immunol. Res. 5(3):182-190 (2017).
Cullis et al., "Macropinocytosis of Nab-paclitaxel byTumor-associated Macrophages Contributes to Macrophage Repolarization in Pancreatic Cancer," (Poster for abstract LB-224) Poster Presentation at AACR Annual Meeting, Apr. 21, 2015.

* cited by examiner

METHODS AND REAGENTS FOR MODULATING MACROPHAGE PHENOTYPE

This application is a division of U.S. patent application Ser. No. 16/306,636, filed Dec. 3, 2018, which is a national stage application under 35 U.S.C. § 371 of International Application No. PCT/US2017/035959, filed Jun. 5, 2017, which claims the priority benefit of U.S. Provisional Patent Application Ser. No. 62/345,591, filed on Jun. 3, 2016, which is hereby incorporated by reference in its entirety.

This application contains a computer readable Sequence Listing, which has been submitted electronically in TXT format and is hereby incorporated by reference in its entirety. Said TXT copy, created on May 27, 2022, is named 147462_001833_ST25.txt and is (8,091 bytes in size.

FIELD OF THE INVENTION

The present invention is directed to methods of modifying the phenotype of macrophages for the treatment of cancer, autoimmune disease, and other conditions where such modification is therapeutic.

BACKGROUND OF THE INVENTION

Pancreatic ductal adenocarcinoma (PDAC) is a lethal disease with a five-year survival rate of less than six percent. A defining feature of PDAC is its prominent desmoplastic reaction with an extensive leukocytic infiltration that is dominated by macrophages (Kurahara et al., "Significance of M2-polarized Tumor-associated Macrophage in Pancreatic Cancer," *J. Surg. Res.* 167: e211-9 (2011)). Depending on signals that prevail within their microenvironment, macrophages can adopt a variety of functional states. In response to bacterial products such as lipopolysaccharide (LPS) and Th1 cytokines, macrophages become immunostimulatory (type-1 phenotype). Type-1 macrophages are characterized by the expression of high levels of nitric oxide synthase (iNOS), major histocompatibility complex II (MHCII), cluster of differentiation 80 and 86 (CD80, CD86), tumor necrosis alpha (TNFα), and can exert a tumoricidal effect (Mantovani et al., "Macrophage Polarization: Tumor-associated Macrophages as a Paradigm for Polarized M2 Mononuclear Phagocytes," *Trends Immunol.* 23:549-55 (2002)). By contrast, in the presence of Th2 cytokines macrophages acquire an alternatively activated state (i.e., a type-2 phenotype) that is immunosuppressive, tumor promoting, and is characterized by the expression of Arginase 1, cluster of differentiation 206 (CD206) and low levels of MHCII (Mantovani et al., "Macrophage Polarization: Tumor-associated Macrophages as a Paradigm for Polarized M2 Mononuclear Phagocytes," *Trends Immunol.* 23:549-55 (2002)). While tumor-associated macrophages (TAMs) in the pancreas exhibit both type-1 and type-2 phenotypes, higher type-2: type-1 ratios correlate with disease progression and shorter survival in patients (Kurahara et al., "Significance of M2-polarized Tumor-associated Macrophage in Pancreatic Cancer," *J. Surg. Res.* 167: e211-9 (2011); Ino et al., "Immune Cell Infiltration as an Indicator of the Immune Microenvironment of Pancreatic Cancer," *Br. J. Cancer* 108:914-23 (2013)).

Abraxane (nab-paclitaxel) is a nanoparticle albumin-bound formulation of paclitaxel that, in combination with gemcitabine, is currently the first line treatment for pancreatic cancer (Von Hoff et al., "Increased Survival in Pancreatic Cancer with Nab-paclitaxel Plus Gemcitabine," *N. Engl. J. Med.* 369:1691-703 (2013)). The primary mechanism of antineoplastic activity of paclitaxel is its ability to stabilize microtubules and prevent cell division of rapidly dividing tumor cells. In macrophages paclitaxel can exert cell cycle-independent effects by acting as an LPS mimetic and inducing macrophage type-1 polarization in a Toll-like receptor 4 (TLR4)-dependent manner (Ding et al., "Taxol Shares the Ability of Bacterial Lipopolysaccharide to Induce Tyrosine Phosphorylation of Microtubule-associated Protein Kinase," *J. Immunol.* 151:5596-602 (1993); Ding et al., "Shared Actions of Endotoxin and Taxol on TNF Receptors and TNF Release," *Science* 248:370-2 (1990); Perera et al., "CD11b/CD18 Acts in Concert with CD14 and Toll-like Receptor (TLR) 4 to Elicit Full Lipopolysaccharide and Taxol-inducible Gene Expression," *J. Immunol.* 166:574-81 (2001)). However, it is unknown whether Abraxane can exert any effect on macrophages in the tumor environment or in the context of other diseases.

The present invention is directed to overcoming these and other deficiencies in the art.

SUMMARY OF THE INVENTION

A first aspect of the present invention is directed to a method of inducing a phenotypic change in a population of monocytes and/or macrophages. This method includes administering to the population of monocytes and/or macrophages, a macrophage stimulating agent coupled to a carrier molecule, wherein the carrier molecule facilitates macropinocytic uptake of the agent by monocytes and macrophages in the population and is defective in neonatal Fc receptor binding. The administration of the macrophage stimulating agent induces a phenotypic change in the monocytes and macrophages in the population.

Another aspect of the present invention is directed to a method of treating a tumor in a subject. This method includes selecting a subject having a tumor and administering to the selected subject an anti-tumor agent coupled to a carrier molecule that is defective in neonatal Fc receptor (FcRn) binding, wherein the administering induces a therapeutic tumor cell response in the subject.

As described herein, the effects of nab-paclitaxel on macrophage polarization were investigated. It is reported that nab-paclitaxel is internalized by macrophages principally via macropinocytosis and is sufficient to drive macrophage type-1 polarization in vitro and in vivo. These data reveal a previously unappreciated mechanism of action of nab-paclitaxel in the tumor context and suggest that nab-paclitaxel could co-operate with immunotherapeutic agents to restore immune recognition of tumor cells. However, given FcRn recycling of albumin, nab-paclitaxel is expelled back out of macrophages reducing its type-1 polarizing effects. The present invention solves this unrecognized problem by coupling paclitaxel to a carrier molecule deficient in FcRn binding to facilitate paclitaxel retention in macrophages to increase its type-1 polarizing effects and enhance its overall therapeutic efficacy in not only pancreatic cancer, but other cancers where tumor-associated macrophages harbor a pro-tumor immunosuppressive phenotype. Similarly, coupling other macrophage stimulating agents as described herein to a carrier molecule that facilitates macropinocytic uptake, but is deficient in FcRn binding has broad applicability in modulating macrophage phenotype in a variety of diseases where type-1/type-2 macrophage tropism influence or contribute to the disease.

BRIEF DESCRIPTION OF THE DRAWINGS

FIG. 1A shows immunofluorescent analysis of RAW 264.7 cells treated for 30 minutes with OG-nab-paclitaxel and TMR-dextran, and FIG. 1B shows cells treated with OG-paclitaxel (left) or OG-nab-paclitaxel (right) and DMSO (vehicle, top) or pretreated with 100 mmol/L EIPA (bottom). FIG. 1C shows cells treated with OG-nab-paclitaxel and PBS (vehicle) or pretreated with anti-CD16/CD32, and FIG. 1D shows cells treated with OG-nab-paclitaxel with DMSO (vehicle) or with BAPTA-AM. All pretreatments were 30 minutes. Macropinocytosis indices are represented graphically in FIGS. 1B-D (right) with bars indicating the SE from at least three independent experiments. *, P<0.05; **, P<0.01.

FIG. 2A shows relative gene expression analysis of Il1α, Il1β, Il6, Il12 p40, and Tnfα normalized to Gapdh in RAW 264.7 cells treated with vehicle (DMSO), LPS, paclitaxel (ptx), or nab-paclitaxel (nab-ptx). FIG. 2B shows relative gene expression levels of Il1α, Il1β, Il6, Il12 p40, and Tnfα treated with nab-ptx alone or with EIPA, BAPTA-AM, or anti-CD16/32. In FIGS. 2A and 2B, bars represent SE from three independent experiments. FIGS. 2C and 2D show western blot analysis of iNOS expression in RAW 264.7 cells. FIG. 2C shows cells treated with vehicle (DMSO), IFNγ, LPS, ptx or nab-ptx alone, or with IFNγ. FIG. 2D shows cells treated with vehicle (DMSO), IFNγ, nab-ptx, or nab-ptx in combination with IFNγ alone or with EIPA. VINCULIN served as a protein loading control. Numbers below Western blots indicate level of iNOS induction normalized to VINCULIN and relative to IFNγ alone. All western blots were cropped using ImageJ to show bands of interest and are representative of at least three independent experiments. Graph in FIG. 2D shows relative gene expression of Inos normalized to Gapdh with bars representing SE from four independent experiments. *, P<0.05; **, P<0.01; ns, not significant FIG. 3A shows relative gene expression levels of Il1α, Il1β, Il6, Il12 p40, and Tnfα treated with nab-ptx alone or with 500 nm CLI-095. Bars represent SE from three independent experiments. *, P<0.05; **, P<0.01; ns, not significant. FIG. 3B shows western blot analysis of iNOS expression in RAW 264.7 cells treated with vehicle (DMSO), IFNγ, or LPS or nab-ptx alone or with IFNγ or with IFNγ and 25 mmol/L CLI-095.

FIG. 4A shows representative hematoxylin and eosin (H&E) and F4/80 immunohistochemistry staining of KPC tumors ten days following implantation into syngeneic mice. Inset shows representative dissected KPC tumor. FIG. 4B shows cryo-immunofluorescent analysis of orthotopic tumors resected 2 weeks after orthotopic implantation and treated ex vivo with 100 mg OG-nab-ptx, followed by immunofluorescent staining with anti-F4/80. Data are representative of three independent experiments. FIG. 4C shows quantification of CD80/CD86-positive cells in KPC orthotopic tumors 48 hours after treatment. Left, the CD80+CD86+ cell population was gated on the CD45+F4/80+MHCII+ cell population. Data are representative of four independent experiments. Right, Representative FACS plot of CD80+CD86+ cell population from PBS (vehicle; left) and nab-paclitaxel (nab-ptx; right)-treated mice are shown. FIG. 4D shows quantification of CD80+IL1α+ cells in KPC orthotopic tumors 48 hours after treatment. Left, CD80+IL1α+ cell population was gated on CD45+F4/80+MHCII+ cell population. Right, Representative FACS plot of CD80+/IL1α+ cell population from PBS (vehicle; left) and nab-paclitaxel (nab-ptx; right)-treated mice are shown. *, P<0.05; **, P<0.01; ns, not significant.

FIG. 7A shows a representative flow cytometry plot of PE-F4/80-positive cells sorted from KPC orthotopic tumors two weeks after orthotopic implantation and treated ex vivo with serum-free medium (vehicle, grey) or 20 μg of OG-nab-ptx (green). Quantification of mean percentage of OG-nab-ptx-positive cells from triplicate samples is shown. Bars depict standard deviation. FIG. 7B shows quantification of total F4/80-positive cells (gated on the CD45-positive population) in KPC orthotopic tumors 48 hours post-treatment. Bars depict standard error from four independent experiments. FIG. 7C shows relative gene expression levels of Il1β in CD45/F4/80 double-positive cells sorted from KPC orthotopic tumors 48 hours post-treatment. *, p<0.05; **, p<0.01; ns, not significant.

DETAILED DESCRIPTION OF THE INVENTION

Figures 1A, 1B:
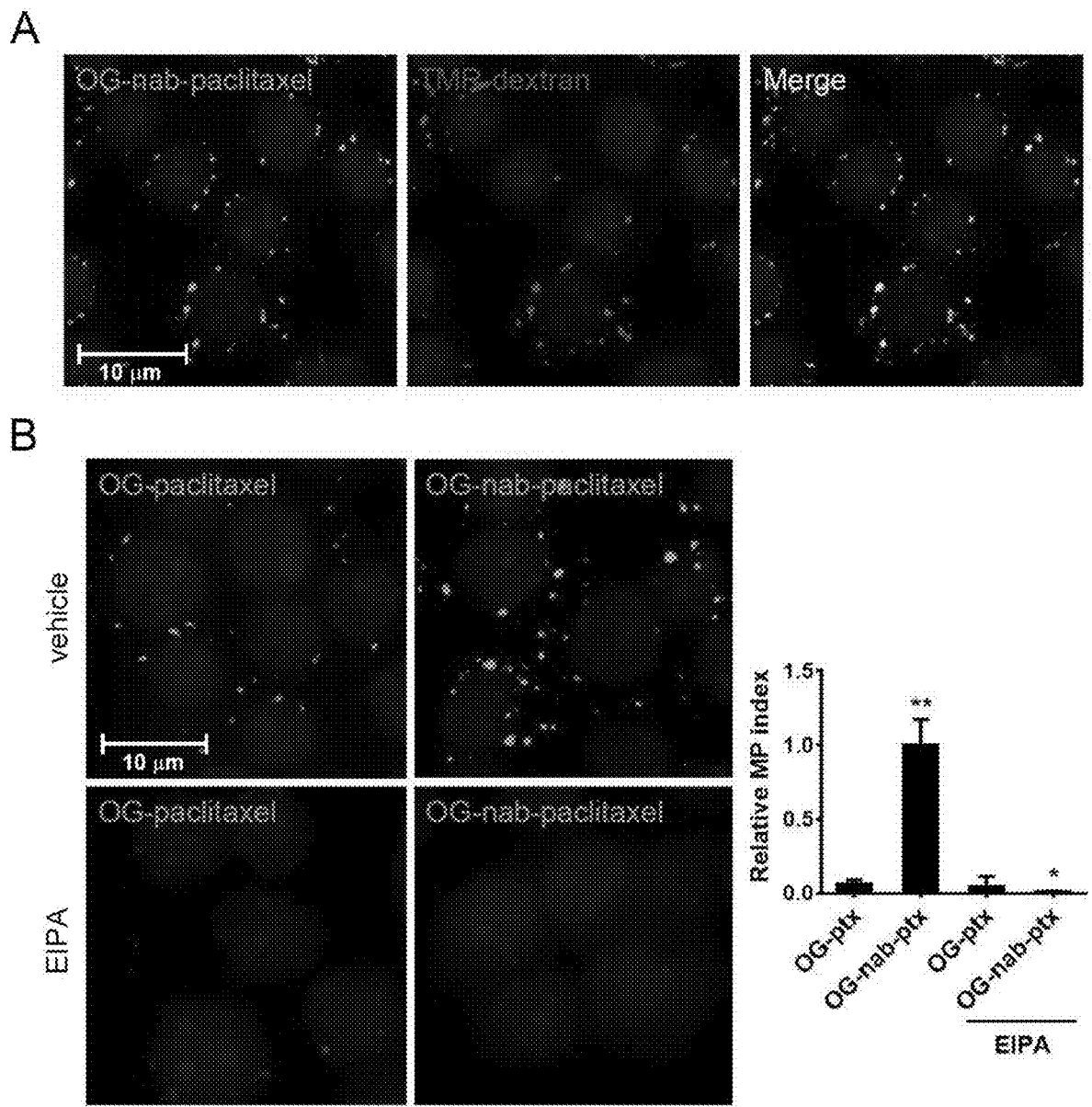
FIGS. 1A-1D demonstrate that macrophages internalize nab-paclitaxel via macropinocytosis.

A first aspect of the present invention is directed to a method of inducing a phenotypic change in a population of monocytes and/or macrophages. The method includes administering to the population of monocytes and/or macrophages, a macrophage stimulating agent coupled to a carrier molecule, where the carrier molecule facilitates macropinocytic uptake of the agent by monocytes and macrophages in the population and is defective in neonatal Fc receptor binding. In accordance with this method, the administered macrophage stimulating agent induces a phenotypic change in the monocytes and macrophages of the population.

Macrophages have historically been divided into two phenotypically diverse populations, i.e., a macrophage type-1-polarized or "classically activated" population, and a macrophage type-2-polarized or "alternatively activated" population. However, it is well appreciated in the art that a continuum of phenotypes exists between the macrophage type-1-polarized and macrophage type-2-polarized populations (e.g., M2a, M2b, and M2c phenotypes), and in some cases macrophages assume a phenotype that does not fit well within any of these defined phenotypic groups (see e.g., Martinez and Gordon, "The M1 and M2 Paradigm of Macrophage Activation: Time for Reassessment," F1000*Prime Rep* 0.6:13 (2014), which is hereby incorporated by reference in its entirety). The methods described herein are suitable for inducing one or more phenotypic changes in a population of monocytes/macrophages to "tune" or "adjust" a population of macrophages/monocytes to have a desired phenotype, e.g., a type-1 phenotype, a type-2 phenotype, a type-2-sub-phenotype, i.e., an M2a, M2b, or M2c phenotype, or any phenotype that falls within the spectrum of known macrophage phenotypes.

Macrophages exhibiting a type-1 phenotype are pro-inflammatory, and are capable of either direct (pathogen pattern recognition receptors) or indirect (Fc receptors, complement receptors) recognition of pathogens and tumor antigens (i.e., they exhibit anti-tumor activity). Type-1 macrophages produce reactive oxygen species and secrete pro-inflammatory cytokines and chemokines, such as, for example, but without limitation, TNFα, IL-1, IL-6, IL-15, IL-18, IL-23, and iNOS. Type-1 macrophages also express high levels of WIC, costimulatory molecules, and FCγR. The type-1 phenotype is triggered by GM-CSF and further stimulated by interferon-γ (IFN-γ), bacterial lipopolysaccharide (LPS), or tumor necrosis factor α (TNFα), and is mediated by several signal transduction pathways involving signal transducer and activator of transcription (STAT), nuclear factor kappa-light-chain-enhancer of activated B cells (NFκB), and mitogen-activated protein kinases (MAPK). These events enhance the production of agents such as the reactive oxygen species and nitric oxide (NO) and promote subsequent inflammatory immune responses by increasing antigen presentation capacity and inducing the Th1 immunity through the production of cytokines such as IL-12.

In contrast, macrophages exhibiting a type-2 phenotype are often characterized as being anti-inflammatory and immunosuppressive as they suppress T-cell responses and are involved in the Th2-type immune response. The type-2 macrophage phenotype facilitates tissue repair, wound healing, and is profibrotic. Type-2 macrophages often undesirably infiltrate and surround tumors, where they provide an immunosuppressive microenvironment that promotes rather than suppresses tumor progression. Type-2 macrophages are characterized by high surface expression of Il-4R, FcεR, Dectin-1, CD136, CD206, and CD209A. Type-2 macrophages include IL-4/IL-13-stimulated macrophages, IL-10-induced macrophages, and immune complex-triggered macrophages.

As used herein, a "phenotypic change" encompasses an observable or detectable change in a characteristic, property, attribute, or function of the macrophages/monocytes in the population. For example, phenotypic characteristics/properties/functions of macrophages/monocytes that can be modified or modulated in accordance with the methods of the present invention include, without limitation, pro-inflammatory activity, anti-inflammatory activity, immunogenic activity, tolerogenic activity, tissue damaging activity, tissue healing activity, cytotoxic activity, migratory activity, bone-resorbing activity, angiogenic activity, anti-angiogenic activity, suppressor activity, antigen presenting activity, or phagocytic activity. A phenotypic change in the monocytes and macrophages may be observed or detected in any of a number of ways. For example, a phenotypic change may be observed or detected either by performing a test, observation, or measurement on the macrophages/monocytes themselves or by performing a test, observation, or measurement, on other cells, tissues, organs, etc., that may be affected by the monocytes/macrophages, or by performing a test, observation, or measurement on a subject that contains the phenotypically modified macrophages.

Phenotypic change or modulation can be assessed by detecting or measuring, for example, (i) a change in the expression of one or more genes (e.g., cytokines, inflammatory mediators, etc.); (ii) the change in secretion of one or more molecules (e.g., cytokines, inflammatory mediators, etc.); (iii) an increase or decrease in migration to one or more sites in the body; (iv) a change in the ability to cause an alteration in one or more phenotypic characteristics or phenotypes of another macrophage-related cell or ability to cause an alteration in one or more phenotypic characteristics or phenotypes of a non-macrophage-related cell.

Methods for observing, detecting, and measuring these phenotypic changes are known in the art and described herein. For example, gene expression profiles can be assessed at the RNA level using cDNA or oligonucleotide microarray analysis, Northern blots, RT-PCR, sequencing, etc. Protein expression can be measured using, for example, immunoblotting, immunohistochemistry, protein microarrays, etc. Various cell-based assays and animal models readily known and utilized in the art can also be used.

As described herein, a "macrophage stimulating agent" can be, for example, a small molecule, a peptide, an oligopeptide, a polypeptide, a protein, an antibody, a synthetic binding molecule, an aptamer, an RNA molecule, a DNA molecule, an oligomer, a polymer, a lipid, or a liposome. In accordance with the methods described herein, the macrophage stimulating agent is delivered to the macrophage via a carrier that facilitates macropinocytic delivery of the agent. Accordingly, the macrophage stimulating agent is one that induces a phenotypic change in monocytes and/or macrophage via an endosome or intracellular signaling pathway. Exemplary classes of molecules that may act as macrophage stimulating agents of the present invention include, without limitation, cytokines, chemokines, pattern recognition receptor ligands, hormones, adrenergic and cholinergic agonists, fatty acids, phospholipids, immunoglobulins or portions thereof, Fc domains of immunoglobulins, lipopolysaccharides (LPS), toll-like receptor (TLR) ligands, histamines, and peroxisome proliferator-activated receptor ligands.

In one embodiment, it is desirable to induce type-1-phenotypic characteristics in a population of monocytes and/or macrophages comprising non-type-1 macrophages, e.g., a population of type-2 macrophages/monocytes or a heterogenous population of type-2 and type-1 macrophages/monocytes. In accordance with this embodiment, a macrophage type-1 stimulating agent coupled to a carrier molecule as described herein is administered to the population of macrophages/monocytes. Suitable macrophage type-1 stimulating agents include, without limitation, paclitaxel, colony stimulating factor-1 (CSF-1) receptor antagonists, IL-10 receptor antagonists, a Toll-like receptor (TLR)-2 agonist, a TLR-3 agonist, a TLR-4 agonist, a TLR-7 agonist, a TLR-8 agonist, and a TLR-9 agonist.

In one embodiment, the macrophage type-1 stimulating agent is paclitaxel. Paclitaxel is a plant derived alkaloid in the taxane family of neoplastic drugs. Paclitaxel mimics LPS and induces the production of IL-12 in macrophages (Mullins et al., "Paclitaxel Enhances Macrophage IL-12 Production in Tumor-bearing Hosts Through Nitric Oxide," *J. Immunol.* 162(11):6811-8 (1999), which is hereby incorporated by reference in its entirety). Derivatives of paclitaxel that similarly induce IL-12 production in macrophages are also suitable for use in accordance with the methods disclosed herein.

In another embodiment, the macrophage type-1 stimulating agent is a CSF-1 receptor antagonist. Suitable CSF-1 receptor antagonists include, without limitation ABT-869 (Guo et al., "Inhibition of Phosphorylation of the Colony-Stimulating Factor-1 Receptor (c-Fms) Tyrosine Kinase in Transfected Cells by ABT-869 and Other Tyrosine Kinase Inhibitors," *Mol. Cancer. Ther.* 5(4):1007-1012 (2006), which is hereby incorporated by reference in its entirety), imatinib (Guo et al., "Inhibition of Phosphorylation of the Colony-Stimulating Factor-1 Receptor (c-Fms) Tyrosine Kinase in Transfected Cells by ABT-869 and Other Tyrosine Kinase Inhibitors," *Mol. Cancer. Ther.* 5(4):1007-1012 (2006), which is hereby incorporated by reference in its entirety), PLX3397 (Mok et al., "Inhibition of CSF1 Receptor Improves the Anti-tumor Efficacy of Adoptive Cell Transfer Immunotherapy," *Cancer Res.* 74(1):153-161 (2014), which is hereby incorporated by reference in its entirety), PLX5622 (Dagher et al., "Colony-stimulating Factor 1 Receptor Inhibition Prevents Microglial Plaque Association and Improves Cognition in 3xTg-AD Mice," *J. Neuroinflamm.* 12:139 (2015), which is hereby incorporated by reference in its entirety), DCC-3014 (Deciphera Pharmaceuticals), BLZ945 (Krauser et al., "Phenotypic and Metabolic Investigation of a CSF-1R Kinase Receptor Inhibitor (BLZ945) and its Pharmacologically Active Metabolite," *Xenobiotica* 45(2):107-123 (2015), which is hereby incorporated by reference in its entirety), and GW2580 (Olmos-Alonso et al., "Pharmacological Targeting of CSF1R Inhibits Microglial Proliferation and Prevents the Progression of Alzheimer's-like Pathology," *Brain* 139:891-907 (2016), which is hereby incorporated by reference in its entirety.

In another embodiment, the macrophage type-1 stimulating agent is an IL-10 receptor antagonist. Suitable IL-10 receptor antagonists include, without limitation peptide antagonists as described in Naiyer et al., "Identification and Characterization of a Human IL-10 Receptor Antagonist," *Hum. Immunol.* 74(1):28-31 (2013), which is hereby incorporated by reference in its entirety, and IL-10 receptor antagonistic antibodies as described in U.S. Pat. No. 7,553,932 to Von Herrath et al., which is hereby incorporated by reference in its entirety.

In another embodiment, the macrophage type-1 stimulating agent is a TLR agonist, i.e., a TLR2, TLR3, TLR4, TLR7, TLR8, or TLR9 agonist. Suitable TLR-2 agonists for use in the methods described herein include Pam3CSK4, a synthetic triacylated lipoprotein, and lipoteichoic acid (LTA) (Brandt et al., "TLR2 Ligands Induce NF-κB Activation from Endosomal Compartments of Human Monocytes" *PLoS One* 8(12): e80743, which is hereby incorporated by reference in its entirety).

A suitable TLR-3 agonist includes, without limitation, polyinosinic:polycytidylic acid (poly I:C) (Smole et al., "Delivery System for the Enhanced Efficiency of Immunostimulatory Nucleic Acids," *Innate Immun.* 19(1):53-65 (2013), which is hereby incorporated by reference in its entirety).

Suitable TLR-4 agonists include, without limitation, MPL (Engel et al., "The Pharmacokinetics of Toll-like Receptor Agonists and the Impact on the Immune System," *Expert Rev. Clin. Pharmacol.* 4(2):275-289 (2011), which is hereby incorporated by reference in its entirety), Glucopyranosyl Lipid-A (Matzner et al., "Perioperative treatment with the new synthetic TLR-4 agonist GLA-SE reduces cancer metastasis without adverse effects," *Int. J. Cancer* 138(7):1754-64 (2016), which is hereby incorporated by reference in its entirety), and Immunomax® (Ghochikyan et al., "Targeting TLR-4 with a novel pharmaceutical grade plant derived agonist, Immunomax®, as a therapeutic strategy for metastatic breast cancer," *J. Trans. Med.* 12:322 (2014), which is hereby incorporated by reference in its entirety)

Suitable TLR-7 agonists include, without limitation, uridine/guanidine-rich single-stranded RNA (Engel et al., "The Pharmacokinetics of Toll-like Receptor Agonists and the Impact on the Immune System," *Expert Rev. Clin. Pharmacol.* 4(2):275-289 (2011), which is hereby incorporated by reference in its entirety), 852A (Dudek et al., "First in Human Phase I Trial of 852A, a Novel Systemic Toll-like Receptor 7 Agonist, to Activate Innate Immune Responses in Patients With Advanced Cancer," *Clin. Cancer Res.* 13(23):7119-7125 (2007), which is hereby incorporated by reference in its entirety), resiquimod (Chang et al., "Topical resiquimod Promotes Priming of CTL to Parenteral Antigens," *Vaccine* 27(42):5791-5799 (2009), which is hereby incorporated by reference in its entirety), imidazoquinolines (Itoh et al., "The Clathrin-mediated Endocytic Pathway Participates in dsRNA-induced IFN-beta Production," *J. Immunol.* 181:5522-9 (2008), which is hereby incorporated by reference in its entirety), ANA975 (Fletcher et al., "Masked oral Prodrugs of Toll-like Receptor 7 Agonists: a New Approach for the Treatment of Infectious Disease," *Curr. Opin. Investig. Drugs* 7(8):702-708 (2006), which is hereby incorporated by reference in its entirety), and imiquimod (Engel et al., "The Pharmacokinetics of Toll-like Receptor Agonists and the Impact on the Immune System," *Expert Rev. Clin. Pharmacol.* 4(2):275-289 (2011), which is hereby incorporated by reference in its entirety).

Suitable TLR-8 agonists include, without limitation, resiquimod (Chang et al., "Topical resiquimod Promotes Priming of CTL to Parenteral Antigens," Vaccine 27(42): 5791-5799 (2009), which is hereby incorporated by reference in its entirety), and imidazoquinolines (Itoh et al., "The Clathrin-mediated Endocytic Pathway Participates in dsRNA-induced IFN-beta Production," *J. Immunol.* 181: 5522-9 (2008), which is hereby incorporated by reference in its entirety), Suitable TLR-9 agonists include, without limitation, CpG-ODN (Yao et al., "Late Endosome/Lysosome-localized Rab7b Suppresses TLR-9-initiated Proinflammatory Cytokine and Type I IFN Production in Macrophages," *J. Immunol.* 183:1751-8 (2009), which is hereby incorporated by reference in its entirety). Specific CpG-ODNs suitable for use are described in Engel et al., "The Pharmacokinetics of Toll-like Receptor Agonists and the Impact on the Immune System," *Expert Rev. Clin. Pharmacol.* 4(2):275-289 (2011), which is hereby incorporated by reference in its entirety.

In accordance with this aspect of the disclosure, administering a macrophage type-1 stimulating agent coupled to a carrier molecule as described herein induces one or more macrophage type-1 phenotypic changes, characteristics, or properties in the macrophages or monocytes of the population. As noted above, these phenotypic changes can be monitored by changes in expression or secretion of one more chemokines, cytokines, or other molecules that typify the macrophage type-1 phenotype. Exemplary markers of the macrophage type-1 phenotype that may be induced and can be monitored include, without limitation, expression, secretion, and/or activity of IL-1α, IL-1β, IL-6, iNOS, IFNγ, IL-12, and TNFα. Accordingly, an increase in the expression or secretion of any one or more of these markers serves to indicate a change in the macrophage phenotype to a type-1 phenotype. Alternatively, the desired phenotypic changes in the population of macrophages/monocytes administered the macrophage type-1 stimulating agent can be monitored by assessing decreases in the expression or secretion of chemokines, cytokines, and other proteins that exemplify the macrophage type-2 phenotype (e.g., IL-10, TGF-β, MRC1, TGM2, CD23, CCL22, and Arginase 1). Methods of detecting and quantifying mRNA and protein expression, protein secretion, or protein activity in cells to monitor phenotypic changes are well known in the art.

In another embodiment, it is desirable to induce macrophage type-2-phenotypic characteristics in a population of monocytes and/or macrophages comprising non-type-2 macrophages, e.g., a population of type-1 macrophages/monocytes or a heterogenous population of type-1 and type-2 macrophages/monocytes. In accordance with this embodiment, a macrophage type-2 stimulating agent coupled to a carrier molecule as described herein is administered to the population. Suitable macrophage type-2 stimulating agents include, without limitation, IL-33, IL-4 receptor agonists, glucocorticoids, IL-10 receptor agonists, and IL-1 receptor agonists.

Suitable IL-4 receptor agonists include, without limitation, mutant IL-4 proteins. Exemplary mutant IL-4 proteins include, but are not limited to those described in U.S. Pat. No. 5,723,118 to Sebald, which is hereby incorporated by reference in its entirety.

Glucocorticoids are a class of corticosteroids, which are well known in the art and suitable for inducing a macrophage type-2 phenotype. Exemplary glucocorticoids for use in the present invention include, without limitation, cortisol, cortisone, prednisone, prednisolone, methylprednisolone, dexamethasone, betamethasone, triamcinolone, beclomethasone, fludrocortisone, deoxycorticosterone, and aldosterone.

IL-10 receptor agonists are also capable of inducing a macrophage type-2 phenotype in accordance with the methods described herein. Suitable IL-10 receptor agonists include, without limitation, mutant IL-10 proteins as described in U.S. Pat. No. 7,749,490 to Sommer et al., which is hereby incorporated by reference in its entirety.

IL-1 receptor agonists are also capable of inducing a macrophage type-2 phenotype in accordance with the methods described herein. Suitable IL-1 receptor agonists include, without limitation, IL-1α, IL-1β, IL-18, IL-33, IL-36α, IL-36β, and IL-36γ (Palomo et al., "The Interleukin (IL)-1 Cytokine Family-Balance Between Agonists and Antagonists in Inflammatory Diseases," *Cytokine* 76(1):25-37 (2015), which is hereby incorporated by reference in its entirety).

In accordance with this aspect of the disclosure, administering a macrophage type-2 stimulating agent coupled to a carrier molecule as described herein induces one or more type-2 phenotypic changes, characteristics, or properties in the macrophages or monocytes of the population. As noted above, these phenotypic changes can be monitored by changes in expression or secretion of one more chemokines, cytokines, or other molecules that typify the macrophage type-2-phenotype or any of the macrophage type-2-phenotype subtypes. Exemplary markers of the macrophage type-2 phenotype include, without limitation, IL-10, TGF-β, MRC1, TGM2, CD23, CCL22, and Arginase 1. Alternatively, the desired phenotypic change(s) in the population of macrophages/monocytes administered the macrophage type-2 stimulating agent are monitored by assessing decreases in the expression or secretion of chemokines, cytokines, and other proteins that exemplify the macrophage type-1 phenotype, e.g., IL-1, IL-6, IL-12, IL-23, and TNFα.

The macrophage type-1 or type-2 stimulating agents described herein are coupled to a carrier molecule for administration in accordance with the methods of the present invention. As noted above, the carrier molecule is a molecule that facilitates macropinocytic uptake of the macrophage stimulating agent by macrophages/monocytes in a population. In addition, the carrier molecule is a molecule that is defective in neonatal Fc receptor binding.

The neonatal Fc receptor (FcRn) is an immunoglobulin G (IgG) receptor as well as a major albumin receptor that is expressed by a variety of cell types in the body, including macrophages and more variably tumor cells. In addition to regulating the internalization of albumin and IgG molecules, FcRn recycles both molecules into the extracellular space. Therefore, in accordance with the methods disclosed herein, where it is desirable to deliver a macrophage stimulating agent to macrophages where the agent is retained inside of the macrophage for purposes of inducing a phenotypic change in the macrophage, the carrier molecule delivering the stimulating agent is one that is deficient or defective in FcRn binding.

In one embodiment, the carrier molecule that facilitates macropinocytic uptake of the macrophage stimulating agent and is defective or deficient in FcRn binding is a variant human albumin protein or fragment thereof. As used herein, the term "variant" albumin means a polypeptide derived from a parent albumin that differs from the parent albumin by one or more amino acid alterations, i.e., a substitution, insertion, and/or deletion, at one or more amino acid residue positions.

As used herein, "albumin" refers to a protein having the same, or very similar three dimensional structure as human serum albumin (HSA) and having a long plasma half-life. Human serum albumin (HSA) is a highly soluble globular protein of $M_r$ 65K and consists of 585 amino acids. HSA is the most abundant protein in the plasma and accounts for 70-80% of the colloid osmotic pressure of human plasma. The amino acid sequence of HSA contains a total of 17 disulphide bridges, one free thiol (Cys 34), and a single tryptophan (Trp 214). In its natural form it is not glycosylated. The amino acid sequence of HSA is shown as SEQ ID NO: 1 below.

```
                                         SEQ ID NO: 1
Asp Ala His Lys Ser Glu Val Ala His Arg Phe Lys Asp
1               5                   10

Leu Gly Glu Glu Asn Phe Lys Ala Leu Val Leu Ile Ala
    15                  20                  25

Phe Ala Gln Tyr Leu Gln Gln Cys Pro Phe Glu Asp His
            30                  35

Val Lys Leu Val Asn Glu Val Thr Glu Phe Ala Lys Thr
40                  45                  50

Cys Val Ala Asp Glu Ser Ala Glu Asn Cys Asp Lys Ser
        55                  60                  65

Leu His Thr Leu Phe Gly Asp Lys Leu Cys Thr Val Ala
                70                  75

Thr Leu Arg Glu Thr Tyr Gly Glu Met Ala Asp Cys Cys
    80                  85                  90

Ala Lys Gln Glu Pro Glu Arg Asn Glu Cys Phe Leu Gln
            95                  100

His Lys Asp Asp Asn Pro Asn Leu Pro Arg Leu Val Arg
105                 110                 115

Pro Glu Val Asp Val Met Cys Thr Ala Phe His Asp Asn
        120                 125                 130

Glu Glu Thr Phe Leu Lys Lys Tyr Leu Tyr Glu Ile Ala
                135                 140

Arg Arg His Pro Tyr Phe Tyr Ala Pro Glu Leu Leu Phe
    145             150                     155

Phe Ala Lys Arg Tyr Lys Ala Ala Phe Thr Glu Cys Cys
            160                 165

Gln Ala Ala Asp Lys Ala Ala Cys Leu Leu Pro Lys Leu
170                 175                 180
```

-continued

```
Asp Glu Leu Arg Asp Glu Gly Lys Ala Ser Ser Ala Lys
        185                 190                 195
Gln Arg Leu Lys Cys Ala Ser Leu Gln Lys Phe Gly Glu
                200                 205
Arg Ala Phe Lys Ala Trp Ala Val Ala Arg Leu Ser Gln
    210                 215                 220
Arg Phe Pro Lys Ala Glu Phe Ala Glu Val Ser Lys Leu
            225                 230
Val Thr Asp Leu Thr Lys Val His Thr Glu Cys Cys His
235                 240                 245
Gly Asp Leu Leu Glu Cys Ala Asp Asp Arg Ala Asp Leu
        250                 255                 260
Ala Lys Tyr Ile Cys Glu Asn Gln Asp Ser Ile Ser Ser
                265                 270
Lys Leu Lys Glu Cys Cys Glu Lys Pro Leu Leu Glu Lys
    275                 280                 285
Ser His Cys Ile Ala Glu Val Glu Asn Asp Glu Met Pro
            290                 295
Ala Asp Leu Pro Ser Leu Ala Ala Asp Phe Val Glu Ser
300                 305                 310
Lys Asp Val Cys Lys Asn Tyr Ala Glu Ala Lys Asp Val
        315                 320                 325
Phe Leu Gly Met Phe Leu Tyr Glu Tyr Ala Arg Arg His
                330                 335
Pro Asp Tyr Ser Val Val Leu Leu Arg Leu Ala Lys
    340                 345                 350
Thr Tyr Glu Thr Thr Leu Glu Lys Cys Cys Ala Ala Ala
            355                 360
Asp Pro His Glu Cys Tyr Ala Lys Val Phe Asp Glu Phe
365                 370                 375
Lys Pro Leu Val Glu Glu Pro Gln Asn Leu Ile Lys Gln
        380                 385                 390
Asn Cys Glu Leu Phe Glu Gln Leu Gly Glu Tyr Lys Phe
                395                 400
Gln Asn Ala Leu Leu Val Arg Tyr Thr Lys Lys Val Pro
    405                 410                 415
Gln Val Ser Thr Pro Thr Leu Val Glu Val Ser Arg Asn
            420                 425
Leu Gly Lys Val Gly Ser Lys Cys Cys Lys His Pro Glu
430                 435                 440
Ala Lys Arg Met Pro Cys Ala Glu Asp Tyr Leu Ser Val
        445                 450                 455
Val Leu Asn Gln Leu Cys Val Leu His Glu Lys Thr Pro
                460                 465
Val Ser Asp Arg Val Thr Lys Cys Cys Thr Glu Ser Leu
    470                 475                 480
Val Asn Arg Arg Pro Cys Phe Ser Ala Leu Glu Val Asp
            485                 490
Glu Thr Tyr Val Pro Lys Glu Phe Asn Ala Glu Thr Phe
495                 500                 505
Thr Phe His Ala Asp Ile Cys Thr Leu Ser Glu Lys Glu
        510                 515                 520
Arg Gln Ile Lys Lys Gln Thr Ala Leu Val Glu Leu Val
                525                 530
Lys His Lys Pro Lys Ala Thr Lys Glu Gln Leu Lys Ala
        535                 540                 545
Val Met Asp Asp Phe Ala Ala Phe Val Glu Lys Cys Cys
                550                 555
Lys Ala Asp Asp Lys Glu Thr Cys Phe Ala Glu Glu Gly
560                 565                 570
Lys Lys Leu Val Ala Ala Ser Gln Ala Ala Leu Gly Leu
        575                 580                 585
```

A number of variant human albumin proteins having reduced FcRn binding or that are deficient in FcRn binding that are suitable for use in the methods described herein have been described in the art. Variant human albumin proteins or fragments thereof having reduced or deficient FcRn include, without limitation, those having one or more amino acid modifications at one or more amino acid positions involved in mediating FcRn binding. These amino acid positions include, without limitation, those corresponding to positions 464, 494, 495, 496, 499, 500, 510, 535, 536, 537, 538, and 573 of SEQ ID NO: 1. Exemplary variant human albumin proteins or fragments thereof comprise an amino acid sequence of SEQ ID NO: 1, or a peptide fragment thereof, with one or more amino acid modifications selected from the group consisting of D494N, D494Q, D494A, E495Q, E495A, T496A, P499A, K536A, P537A, K538A, K500A, K573STOP, H464Q, H510Q, and H535Q.

Additional exemplary variant albumin proteins include those comprising mutations at the C-terminus of albumin, including K574, Q580, N111, and D108 (see U.S. Pat. No. 8,822,417 to Andersen et al., which is hereby incorporated by reference in its entirety), and variants comprising mutations at position E492 as described by U.S. Patent Application Publication No. 2016/0009787 to Sleep et al., which is hereby incorporated by reference in its entirety. Other variant albumin proteins or fragments thereof that have reduced or defective binding to FcRn and are suitable for use in the methods described herein are disclosed in U.S. Pat. No. 8,314,156 to Desai et al., U.S. Patent Application Publication No. 2012/0220530 to Plumridge et al., U.S. Patent Application Publication No. 2016/0009787 to Sleep et al., U.S. Patent Application Publication No. 2015/0210752 to Cameron et al., WO2011/051489 to Plumridge et al., WO2012/150319 to Andersen et al., U.S. Patent Application Publication No. 2012/0076728 to Wu et al., and U.S. Patent Application Publication No. 2014/0315816 to Andersen et al., which are hereby incorporated by reference in their entirety.

In another embodiment, the carrier molecule that facilitates macropinocytic uptake of the macrophage stimulating agent and is defective or deficient in FcRn binding is a variant human immunoglobulin G (IgG) protein or fragment thereof. As used herein, a "variant" human IgG protein or fragment encompasses a polypeptide derived from a parent IgG that differs from the parent IgG by one or more amino acid alterations, i.e., substitution, insertion, and/or deletion, at one or more positions. FcRn binds with high affinity to the heavy chain constant regions (CH2 and CH3) of the Fc-region of an IgG. Accordingly, variants of IgG with reduced FcRn binding preferably contain one or more amino acid alterations within the CH2 and/or CH3 region of the Fc portion.

Variant human immunoglobulin G proteins or fragments thereof that are defective in FcRn binding and suitable for use in accordance with the methods described herein have been described in the art. Exemplary variant IgG proteins include those having an amino acid substitution as one or more amino acid positions selected from 252, 255, 282, 309, and 434 (numbering of the IgG heavy chain residues is according to the Kabat EU index numbering system; Kabat et al., "Sequences of Proteins of Immunological Interest" NIH Publication No 91-3242 (1991), which is hereby incorporated by reference in its entirety). By way of example, IgG proteins comprising at least one mutation at M252T, R255D, V282R, V282D, V282E, V282K, L309R, L309D, L309K, L309E, or N434L of the Fc portion of IgG1 are suitable for use in the methods described herein (see U.S. Patent Application Publication No. 2007/0148164 to Farrington et al., which is hereby incorporated by reference in its entirety). Other suitable variant IgG proteins include, without limitation, those described in U.S. Pat. No. 8,802,820 to Chamberlain et al., and WO2016/071377 to Schlothauer et al., which are hereby incorporated by reference in their entirety.

Modulating or modifying macrophage/monocyte phenotype as described herein is carried out for the purpose of treating, preventing, or slowing the progression of a disease or condition that is caused or exacerbated, at least in part, by macrophages exhibiting one or more undesirable phenotypic characteristics or phenotypes. For example, inflammatory diseases and conditions, including but not limited to macular degeneration, atherosclerosis, osteoporosis, immune inflammation, non-immune inflammation, renal inflammation, tuberculosis, multiple sclerosis, arthritis, chronic obstructive pulmonary disease (COPD), and Alzheimer's disease, involve the undesired actions of type-1 macrophages. Employing the methods of the present invention to induce a macrophage type-2 phenotypic change in the type-1 pro-inflammatory macrophages that are involved in or contributing to these disease processes alleviates one or more symptoms or causes of the disease. Accordingly, in one embodiment, the administering is carried out in vivo or ex vivo as described infra to a population of type-1 macrophages in or from a subject having an inflammatory or autoimmune condition, including, but not limited to any of those enumerated above. Administering a type-2 macrophage stimulating agent to a population of type-1 macrophages in this context will induce a type-2 phenotypic change, thereby reducing the undesired actions of the type-1 macrophages associated with the disease.

Modulating or modifying macrophage/monocyte phenotype is also therapeutically beneficial in context of treating various forms of cancer. Recent studies indicate that tumor-associated macrophages (TAMs) exhibit a macrophage type-2-like phenotype. These type-2 macrophages are important tumor-infiltrating cells and play pivotal roles in tumor growth and metastasis. In most solid tumors, the existence of TAMs is advantageous for tumor growth and metastasis. These TAMs produce interleukin IL-10 and transforming growth factor (TGF)β to suppress general antitumor immune responses. Meanwhile, TAMs promote tumor neo-angiogenesis by the secretion of pro-angiogenic factors and define the invasive microenvironment to facilitate tumor metastasis and dissemination. Therefore, employing the methods of the present invention to induce a type-1 phenotypic change in the TAMs to enhance anti-tumor immunity will significantly alter the progression of the cancer. Cancers that typically have a type-2 macrophage-related component include, without limitation, pancreatic cancer, breast cancer, and non-small cell lung cancer. Accordingly, in one embodiment, administering a macrophage stimulating agent, e.g., a macrophage type-1 stimulating agent, is carried out in vivo or ex vivo as described in more detail below, to a population of type-2 macrophages in or from a subject having cancer, where the cancer is characterized as having an immunosuppressive microenvironment. As noted above, such cancers include, without limitation pancreatic cancer, breast cancer, and non-small cell lung cancer.

In one embodiment of this aspect of the invention, the administration of a macrophage type-1 simulating agent is combined with a T-cell immunotherapy to boost the patient's anti-tumor immune response. Suitable T-cell immunotherapies include, without limitation, adoptive T-cell therapy, tumor-infiltrating lymphocyte therapy, chimeric antigen receptor (CAR) T-cell therapy, and antigen-specific T-cell receptor transduced T-cell therapy.

Accordingly, in practicing the methods described herein, the administering step can be carried out in vitro, ex vivo, or in vivo. For example, in certain embodiments, it is desirable to obtain a population of macrophages/monocytes from a subject, administer the macrophage stimulating agent to the population of macrophages/monocytes ex vivo under conditions suitable for one or more phenotypic changes to occur, and then transplant, inject, or implant the phenotypically modified macrophages into the subject in need thereof (see e.g., Ferenback and Kluth, "Macrophage Cell Therapy in Renal Disease," *Semin. Nephrol.* 30(3): 345-53 (2010), and Rybalko et al., "The Development of Macrophage-Mediated Cell Therapy to Improve Skeletal Muscle Function after Injury," *PLoS One* 10(12): e0145550 (2015), which are hereby incorporated by reference in their entirety).

In another embodiment, the macrophage stimulating agent can be administered in vivo to a subject in need thereof. Such administration can be carried out systemically. By way of example, suitable modes of systemic administration include, without limitation, orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes. Alternatively, the in vivo administration can be carried out via local administration. Suitable modes of local administration include, without limitation, catheterization, implantation, direct injection, dermal/transdermal application, stenting, ear/eye drops, or portal vein administration to relevant tissues, or any other local administration technique, method or procedure, as is generally known in the art. In the context of treating cancer, for example, local administration to the tumor site can be carried out to selectively modify or induce a type-1-macrophage phenotype in macrophages of the tumor microenvironment.

In accordance with this and all other aspects of the present invention, a "subject", "patient", or "individual" that is amendable to treatment using the methods described herein includes any animal. In one embodiment, the subject is a mammal. In another embodiment, the subject is a human.

Another aspect of the present invention is directed to compositions comprising the macrophage stimulating reagent coupled to a carrier molecule, where the carrier molecule is taken up by macrophages and/or monocytes via macropincytosis and is defective in neonatal Fc receptor binding. Suitable macrophage type-1 and type-2 stimulating reagents are described supra. Suitable carrier molecules include modified or variant human albumin proteins and peptides, where said modification or variant is one that reduces or eliminates albumin binding to FcRn. Suitable modified albumin proteins and peptides are disclosed supra. Other suitable carrier molecules include modified or variant IgG proteins or peptides, where said modification or variant is one that reduces or eliminates IgG binding affinity to FcRn. Suitable IgG variants are disclosed supra.

Pharmaceutical compositions containing the macrophage stimulating agents coupled to the a carrier molecule having reduced or deficient FcRN binding affinity of the present invention can be formulated as necessary according to the intended route of administration. For example, for compositions administered orally, the macrophage stimulating agent couple to the carrier molecule is mixed with an inert diluent, or with an assimilable edible carrier, or it may be enclosed in hard or soft shell capsules, or it may be compressed into tablets, or they may be incorporated directly with the food of the diet. Agents of the present invention may also be administered in a time release manner incorporated within such devices as time-release capsules or nanotubes. Such devices afford flexibility relative to time and dosage. For oral therapeutic administration, the agents of the present invention may be formulated with excipients and used in the form of tablets, capsules, elixirs, suspensions, syrups, and the like. Such compositions and preparations should contain at least 0.1% of the agent, although lower concentrations may be effective and indeed optimal. The percentage of the agent in these compositions may, of course, be varied and may conveniently be between about 2% to about 60% of the weight of the unit. The amount of an agent of the present invention in such therapeutically useful compositions is such that a suitable dosage will be obtained.

When the macrophage stimulating agents of the present invention are administered parenterally, solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

Pharmaceutical formulations suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver the agents of the present invention systemically, they may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Intraperitoneal or intrathecal administration of the agents of the present invention can also be achieved using infusion pump devices. Such devices allow continuous infusion of desired compounds avoiding multiple injections and multiple manipulations.

Compositions containing a macrophage stimulating agent coupled to an appropriate carrier molecule of the present invention may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

Effective doses of the compositions of the present invention, for the therapeutic treatment (e.g., therapeutic treatment of inflammatory conditions or cancer) vary depending upon many different factors, including type and stage of the disease, means of administration, target site, physiological state of the patient, other medications or therapies administered, and physical state of the patient relative to other medical complications. Treatment dosages need to be titrated to optimize safety and efficacy.

Another aspect of the present invention is directed to a method of treating a tumor in a subject. This method involves selecting a subject having a tumor and administering to the selected subject an anti-tumor agent coupled to a carrier molecule that is defective in neonatal Fc receptor (FcRn) binding, wherein the administering induces a therapeutic tumor cell response in the subject.

In accordance with this embodiment, the tumor is characterized by tumor cells expressing FcRn. Exemplary tumor types that exhibit FcRn expression include, without limitation, tumors of the lung, colon, pancreas, and glioblastoma multiforme. As noted above, the FcRn binds to and actively recycles albumin and IgG molecules. Therefore, the activity of an anti-tumor cell agent that is coupled to an albumin carrier molecule (such as nanoparticle albumin bound paclitaxel) or fused to an IgG will be enhanced if coupled to a variant albumin protein or variant IgG that is defective or deficient in FcRn binding so as to prevent or reduce FcRn mediate recycling of the anti-tumor agent out of the cell. For example, nanoparticle albumin bound paclitaxel (nab-paclitaxel, trade name Abraxane) is a human albumin bound formulation of paclitaxel that is approved by the FDA as a first line therapy for advanced pancreatic cancer. Paclitaxel's primary mechanism of anti-neoplastic activity is its ability to stabilize microtubules and prevent cell division of rapidly dividing tumor cells. However, some KRas-mutant pancreatic cancer cells express FcRn. Therefore, these cells escape the cytotoxic effects of nab-paclitaxel, resulting in decreased tumor cell killing. Accordingly, in one embodiment, a subject having pancreatic cancer, in particular pancreatic ductal adenocarcinoma (PDAC), is selected and administered an anti-tumor agent that is coupled to a carrier molecule defective in FcRn binding.

In one embodiment, the method of treating a tumor in a subject as described herein further involves selecting a subject suitable for treatment by detecting the presence or absence of FcRn expression in the tumor cells. Subjects having a tumor, where the tumor cells are positive for FcRn expression would benefit from treatment with an anti-tumor agent that is coupled to a carrier molecule defective in FcRn binding. Methods and modes of administering agents of the present invention are described supra.

As used herein, the term "anti-tumor agent" encompasses any reagent that acts directly on or in a tumor cell to inhibit tumor cell division and/or cause tumor cell death. These agents include, without limitation, chemotherapeutic agents such as, alkylating agents (e.g., chlorambucil, cyclophophamide, CCNU, melphalan, procarbazine, thiotepa, BCNU, and busulfan), antimetabolites (e.g., methotraxate, 6-mercaptopurine, and 5-fluorouracil), anthracyclines (daunorubicin, doxorubicin, idarubicin, epirubicin, and mitoxantrone), antitumor antibiotics (e.g., bleomycin, monoclonal antibodies (e.g., Alemtuzumab, Bevacizumab, Cetuximab, Gemtuzumab, Ibritumomab, Panitumumab, Rituximab, Tositumomab, and Trastuxmab), platiniums (e.g., cisplatin and oxaliplatin) or plant alkaloids (e.g., topoisomerase inhibitors, vinca alkaloids, taxanes (e.g. paclitaxel), and epipodophyllotoxins). As indicated above, coupling an antitumor cell agent to a carrier molecule that is defective or deficient in FcRn binding (e.g., variant albumin or variant IgG proteins or fragments thereof) will enhance the activity of the reagent on the target tumor cells to induce a therapeutic tumor cell response, i.e., inhibition of tumor cell division or induction of tumor cell death.

EXAMPLES

The following examples are provided to illustrate embodiments of the present invention but they are by no means intended to limit its scope.

Material and Methods for Examples

Cell lines and cell culture treatments. All cells were maintained under 5% $CO_2$ at 37° C. and cultured in DMEM (Gibco) supplemented with 10% FBS (Gibco), penicillin and streptomycin (Gibco), and 25 mmol/L HEPES (Gibco). Mouse RAW 264.7 cells were obtained from the American Type Culture Collection (2014, ATCC TIB-71). Mouse KPC cells were a kind gift from Dr. R. H. Vonderheide (2013) and generated as previously described (Lo et al., "Tumor-Promoting Desmoplasia Is Disrupted by Depleting FAP-Expressing Stromal Cells," *Cancer Res.* 75:2800-10 (2015), which is hereby incorporated by reference in its entirety). Cell lines were not authenticated and were tested for mycoplasma contamination every 3 months by DAPI stain of cells grown for 1 week in the absence of antibiotics. KPC and RAW 264.7 were propagated for 2 to 3 passages (approximately 1 week) prior to use in all experiments and were kept in culture for no longer than 1 month. Recombinant mouse interferon gamma IFNγ was purchased from R&D Systems (CN 485 MI/CF), LPS (L2630), and paclitaxel (T7402) were purchased from Sigma-Aldrich, CLI-095 was purchased from Invivogen (TLRL-CLI95), BAPTA-AM was purchased from Life Technologies (B6769), and 5-(N-ethyl-N-isopropyl) amiloride (EIPA) was purchased from Invitrogen Molecular Probes (e-3111). Reagents were used at concentrations of 5 ng/mL (IFNγ), 20 ng/mL (LPS), 10 mmol/L (paclitaxel), 500 nmol/L (CLI-095), 50 mmol/L (BAPTA-AM), and 50 mmol/L (EIPA) unless indicated otherwise. Tetramethylrhodamine (TMR)-labeled dextran was purchased from Invitrogen (D1822). Nab-paclitaxel (Abraxane; Abraxis BioScience) pharmaceutical grade powder was purchased through the NYU Langone Medical Center pharmacy and used at a concentration of 10 mmol/L for in vitro experiments.

Antibodies. Antibodies used for western blotting are as follows: rabbit anti-IL1α, rabbit anti-IL1β (Abcam ab9722), rabbit anti-IL6 (Novus Biologicals NB600-1131), rabbit anti-iNOS (Cell Signaling Technology, CST 13120), rabbit anti-TNFα (Abcam ab9739), and mouse anti-VINCULIN (Sigma V9131). F4/80 antibody used for immunofluorescence and immunohistochemistry was purchased from eBiosciences (rat anti-mouse F4/80, clone BM8, ref 14-480182). CD16/CD32 antibody was purchased from BD Biosciences (rat anti-mouse-CD16/CD32, clone 2.4G2) and used at a concentration of 25 mg/mL. Monoclonal antibodies used for flow cytometry were all purchased from Biolegend unless indicated otherwise: anti-CD45 (Brilliant Violet 421-anti-mouse-CD45, clone 30-F11), anti-F4/80 (PE-anti-mouse-F4/80, clone BM8 or APC-anti-mouse-F4/80, clone BM8), anti-MHCII (FITC-anti-mouse-I-A/I-E, clone M5/114.15.2, BD Biosciences), anti-CD80 (PE/Cy7-anti-mouse-CD80, clone 16-10A1), anti-CD86 (PerCP-anti-mouse-CD86, clone GL-1), and anti-IL1a (PE-anti-mouse-IL1α, clone ALF-161).

Western blot analysis. Western blot analyses were initiated 24 hours (iNOS) or 8 hours (IL1α, IL1β, IL6, and TNFα) following cell culture treatments. Total cell lysates were harvested in sample buffer (40 mmol/L Tris, pH 6.8, 1% SDS, 5% beta-mercaptoethanol, 7.5% glycerol, and 0.01% bromophenol blue) and incubated at 99° C. for 5 minutes. Cell lysates (1/10 of total volume) were loaded onto 10% SDS-Polyacrylamide gels for electrophoresis and transferred onto nitrocellulose membranes for 1 hour at 100 volts at 4° C. Membranes were blocked for 1 hour at room temperature in 5% BSA (Sigma-Aldrich) diluted in PBS containing 0.1% Tween 20 prior to immunodetection.

Gene expression analysis. For in vitro qPCR analysis, total RNAwas harvested 2 hours (IL1α, IL1β, IL6, TNFα, and iNOS) or 8 hours (IL12β) after cell culture treatments, using the QIAGEN RNA extraction Kit (QIAGEN). For in vivo gene expression analysis, the CD45 F4/80 double-positive population was sorted directly into TRIzol LS Reagent (Thermo-FisherScientific; CN 10296) from dissociated orthotopic tumors 48 hours after treatment, and total RNA was purified according to the manufacturer's protocol. Purified RNA (1 mg) was reverse-transcribed using the QuantiTect Reverse Transcription Kit (QIAGEN), and 1 of 10 of cDNA mixture (in vitro experiments) or 1 of 3 of cDNA mixture (in vivo experiments) was used for qPCR reaction. Primers were obtained from Integrated DNA Technologies (IDT) with the following sequences (5'-3'): Il1α (Forward) AATCAAGATGGCCAAAGTTCC (SEQ ID NO: 2), (Reverse) ATTCAGAGAGAGATGGTCAATGG (SEQ ID NO: 3); Il1β (Forward) GCAACTGTTCCT-GAACTCAACT (SEQ ID NO: 4), (Reverse) ATCTTTTGGGGTCCGTCAACT (SEQ ID NO: 5); Il6 (Forward) TAGTCCTTCCTA-CCCCAATTTCC (SEQ ID NO: 6), (Reverse) TTGGTCCTTAGCCACTCCTTC (SEQ ID NO: 7); Inos (Forward) GTTCTCAGCCCAACAATA-CAAGA (SEQ ID NO: 8), (Reverse) GTGGACGGGTC-GATCTCAC (SEQ ID NO: 9); Tnfα (Forward) CTGTAGCCCACGTCGTAGC (SEQ ID NO: 10), (Reverse) TTGAGATCCATGCCGTTG (SEQ ID NO: 11); Il12b (Il12 p40) (Forward) TGGTTTGC-CATCGTTTTGCTG (SEQ ID NO: 12), (Reverse) ACAGGTGA-GGTTCACTGTTTCT (SEQ ID NO: 13); Gapdh (Forward) CACGGCAAATTCAACGGCACAGTC (SEQ ID NO: 14), (Reverse) ACCCGTTTGGCTC-CACCCTTCA (SEQ ID NO: 15); Rps29 GTCT-GATCCGCAAATACGGG (SEQ ID NO: 16) (Forward), AGCCTATGTCCTTC-GCGTACT (SEQ ID NO: 17) (Reverse).

Synthesis of Oregon green-labeled paclitaxel and nab-paclitaxel. Albumin-bound Oregon Green 488-labeled paclitaxel (OG-nab-paclitaxel) was prepared by coupling Oregon Green 488-labeled paclitaxel (OG-paclitaxel; Thermo Fisher Scientific, CN P22310) to human serum albumin (Sigma-Aldrich; CN 05420). Briefly, 0.9 mg OG-paclitaxel was dissolved in 64.8 mL chloroform and 7.2 mL ethanol and added to 18 mg human serum albumin dissolved in 3.6 mL water with vigorous stirring. The suspension was sonicated at 40% amplitude for 4 cycles of 1 minute each with 30-second intervals. The organic solvent was then evaporated using rotavapor at 40° C. The resulting suspension was distributed equally into glass vials and lyophilized to obtain dry OG-nab-paclitaxel amenable to long-term storage at −20° C.

Macropinocytosis assays. Macropinocytosis assays, image acquisition, image processing tools, and macropinosome quantification were performed as previously described (Commisso et al., "Determining the Macropinocytic Index of Cells Through a Quantitative Image-based Assay," *Nat. Protoc.* 9:182-92 (2014), which is hereby incorporated by reference in its entirety). For ex vivo nab-paclitaxel uptake assays, orthotopic tumors were cut into approximately 3 mm×3 mm sections and incubated for 20 minutes at 37° C. in serum-free medium containing Oregon Green-labeled nab-paclitaxel (0.5 mg/mL). Tumor sections were then washed once with PBS at room temperature and immediately embedded in Tissue-Tek OCT medium (VWR) and fixed for 1 hour on dry ice. Fixed tumor sections were stored at −80° C. until cryosectioned and mounted on coverslips to be stained for immunofluorescence.

Immunohistochemistry. Immunohistochemistry on tumor sections was performed as previously described (Pylayeva-Gupta et al., "Oncogenic Kras-induced GM-CSF Production Promotes the Development of Pancreatic Neoplasia," *Cancer Cell* 21:836-47 (2012), which is hereby incorporated by reference in its entirety).

Cell sorting and flow cytometry. Staining for cell sorting and flow cytometry analysis was performed by incubating single-cell suspensions with primary fluorochrome-labeled antibodies on ice for 30 minutes. For cell sorting, cells were washed once with FACS buffer (PBS supplemented with 1% FBS) and immediately sorted on an SY2300 cell sorter (Sony). For flow cytometry, cells were fixed in 3.7% formaldehyde diluted in FACS buffer overnight at 4° C. prior to analysis. For IL1a staining, cells were permeabilized and fixed with FoxP3/Transcription Factor Staining Buffer Set (eBioscience CN00-5523) for 45 minutes at 4° C. and stained overnight at 4° C. All samples were washed once with FACS buffer prior to analysis on an LSRII UV flow cytometer (BD Biosciences). Collected data were analyzed using FlowJo data analysis software (V10).

Animal studies. All animals used in this study were 8-week-old C57/BL6 female mice purchased from Charles River Laboratories. For orthotopic implantations, 1×10$^5$ KPC cells were resuspended in 20 μL cold PBS and mixed with 20 μL Matrigel (Corning; ref 254348) prior to injection into the pancreas of syngeneic mice. After 2 weeks, orthotopically implanted mice were treated intraperitoneally with gemcitabine (120 mg/kg, Gemzar, Eli Lilly) and nab-paclitaxel (120 mg/kg, Abraxane; Abraxis Bioscience) resuspended in sterile PBS. Both drugs were purchased through the NYU Langone Medical Center pharmacy. All animal care and procedures were approved by the Institutional Animal Care and Use Committee at the NYU School of Medicine.

Statistical analyses. Statistical comparisons were evaluated by the Student t test. All P values stated are intentionally presented as uncorrected for multiple comparisons, as one planned comparison was conducted for each experimental condition tested (i.e., multiple comparisons were not performed).

Example 1—Macrophages Internalized Nab-Paclitaxel Via Macropinocytosis

Figure 1C:
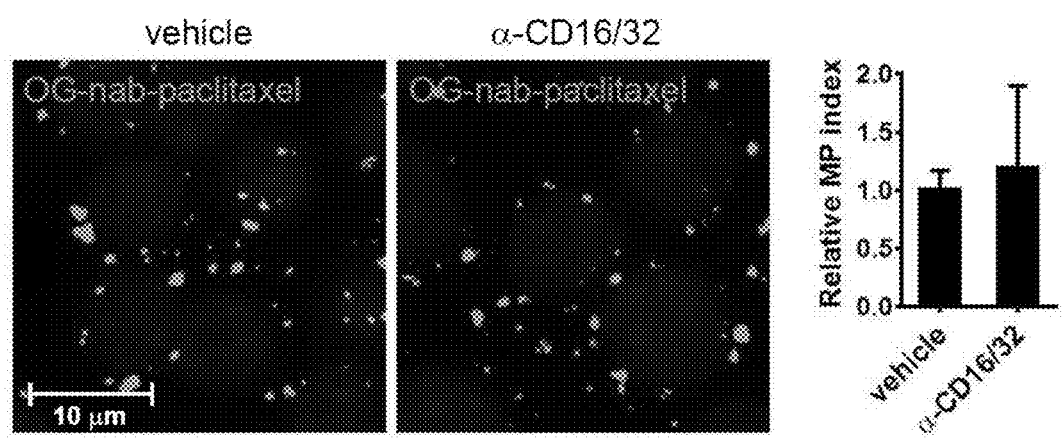
Figure 1D:
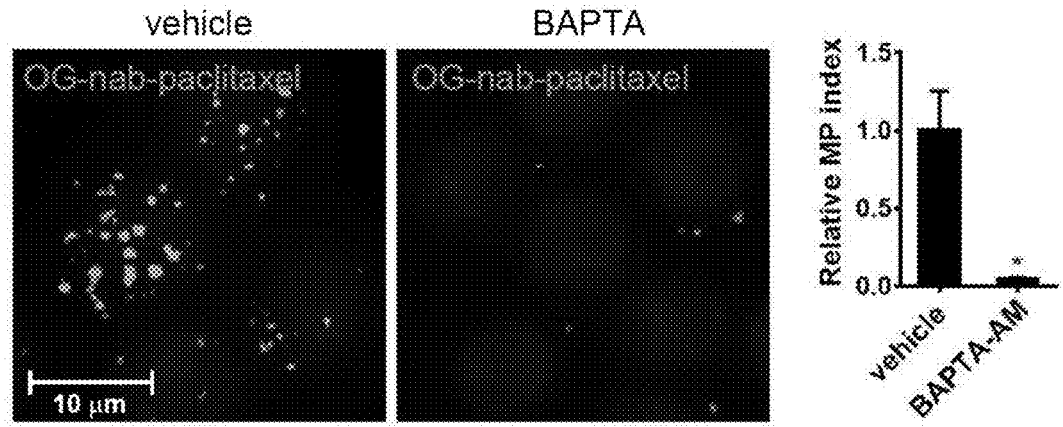

Macrophages undergo constitutive macropinocytosis, a form of nonselective fluid-phase endocytosis that, together with receptor-activated phagocytosis, regulates antigen sampling and scavenging of invading pathogens (Sallusto et al., "Dendritic Cells Use Macropinocytosis and the Mannose Receptor to Concentrate Macromolecules in the Major Histocompatibility Complex Class II Compartment: Downregulation by Cytokines and Bacterial Products," *J. Exp. Med.* 182:389-400 (1995), which is hereby incorporated by reference in its entirety). Macropinocytosis is also an established route of internalization of many nanoparticle formulations (Lim et al., "Macropinocytosis: An Endocytic Pathway for Internalising Large Gulps," *Immunol. Cell Biol.* 89:836-43 (2011), which is hereby incorporated by reference in its entirety). Given that macrophages constitute a dominant immune infiltrate in PDAC, the extent and mode of nab-paclitaxel internalization by macrophages was assessed. To this end, the macrophage cell line RAW 264.7 was incubated with high molecular weight TMR-labeled dextran (TMR-dextran), an established marker of macropinosomes, and Oregon Green-labeled nab-paclitaxel (OG-nab-paclitaxel). OG-nab-paclitaxel localized predominantly to dextran-positive macropinosomes (FIG. 1A). Furthermore, OG-nab-paclitaxel internalization was reduced following treatment with the macropinocytosis inhibitor 5-[N-ethyl-N-isopropyl] amiloride (EIPA), indicating that nab-paclitaxel internalization depended on a macropinocytotic uptake mechanism (FIG. 1B). To determine the contribution of phagocytosis to nab-paclitaxel internalization, the requirement of Fc receptors for uptake was tested because, unlike other major phagocytic receptor families, Fc receptors are constitutively active in macrophages (Ravetch JV, "Fc Receptors: Rubor Redux," *Cell* 78:553-60 (1994), which is hereby incorporated by reference in its entirety). Inhibition of Fc receptors I and III with blocking antibodies to CD16 and CD32 (Indik et al., "The Molecular Dissection of Fc Gamma Receptor Mediated Phagocytosis," *Blood* 86:4389-99 (1995), which is hereby incorporated by reference in its entirety) did not affect the internalization of OG-nab-paclitaxel (FIG. 1C). Moreover, depletion of intracellular calcium, required for constitutive macropinocytosis but not Fc receptor-dependent phagocytosis in macrophages (Di Virgilio et al., "Fc Receptor-mediated Phagocytosis Occurs in Macrophages at Exceedingly Low Cytosolic Ca2+ Levels," *J. Cell Biol.* 106:657-66 (1988); Jongstra-Bilen et al., "Fcgamma-receptors Induce Mac-1 (CD11b/CD18) Mobilization and Accumulation in the Phagocytic Cup for Optimal Phagocytosis," *J. Biol. Chem.* 278:45720-9 (2003), which are hereby incorporated by reference in their entirety), effectively blunted OG-nab-paclitaxel uptake (FIG. 1D). Together, these data demonstrate that nab-paclitaxel is internalized by macrophages predominantly via macropinocytosis.

Example 2—Macropinocytosis of Nab-Paclitaxel Drove M1 Macrophage Activation In Vitro Via TLR4

Figure 2A:
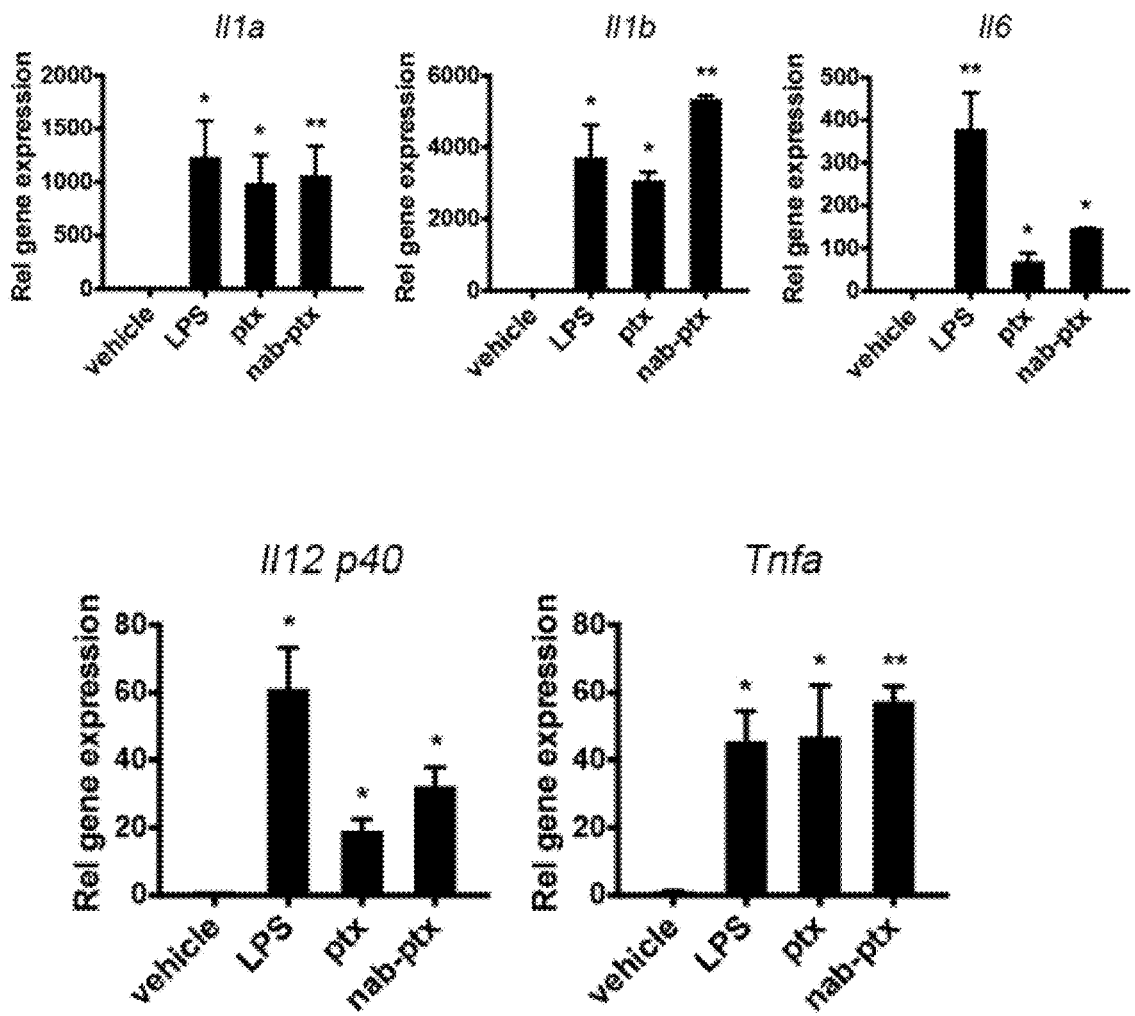
FIGS. 2A-2D show that nab-paclitaxel drives M1 macrophage activation in vitro.
Figure 2B:
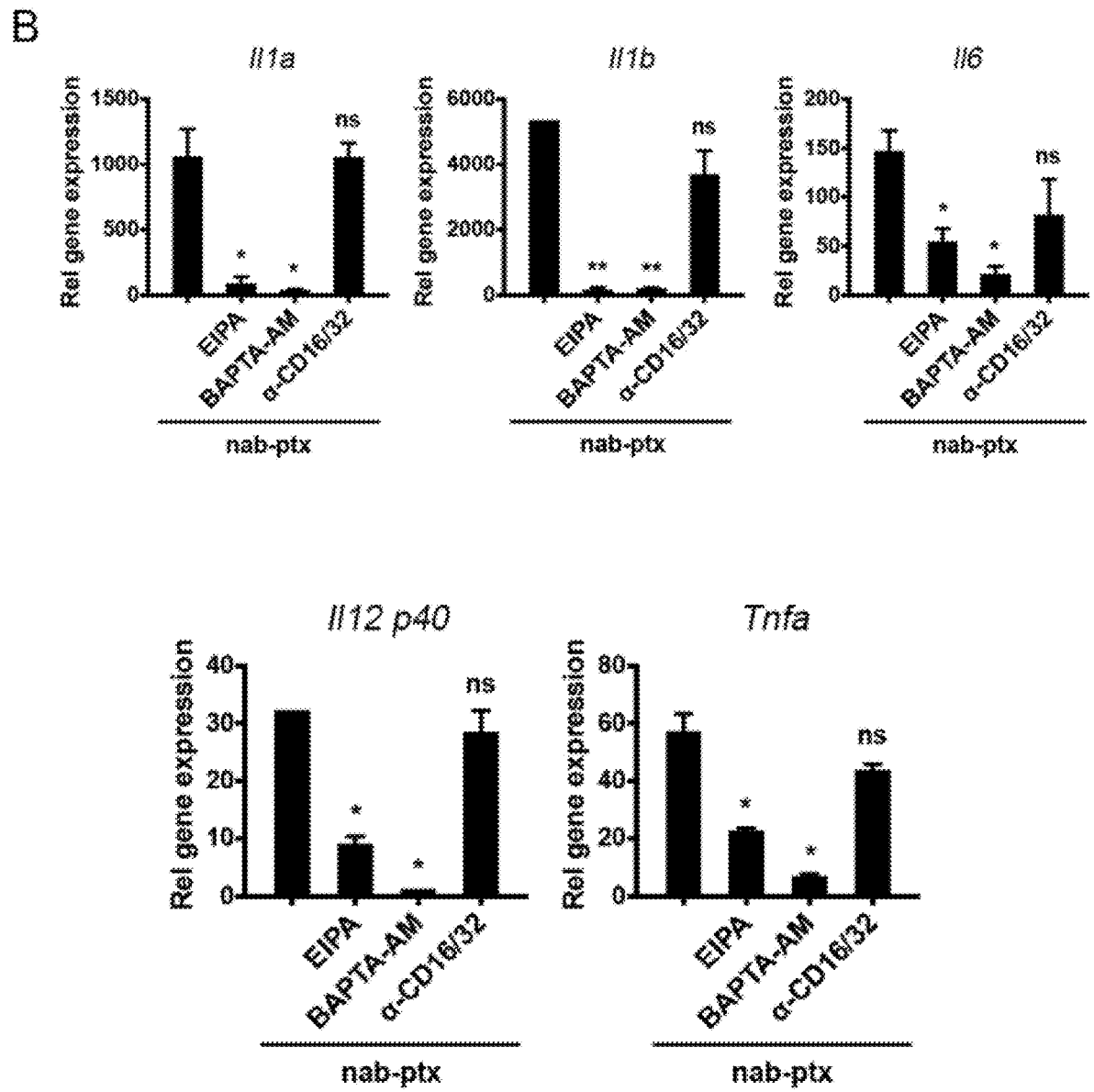
Figures 2C, 2D:
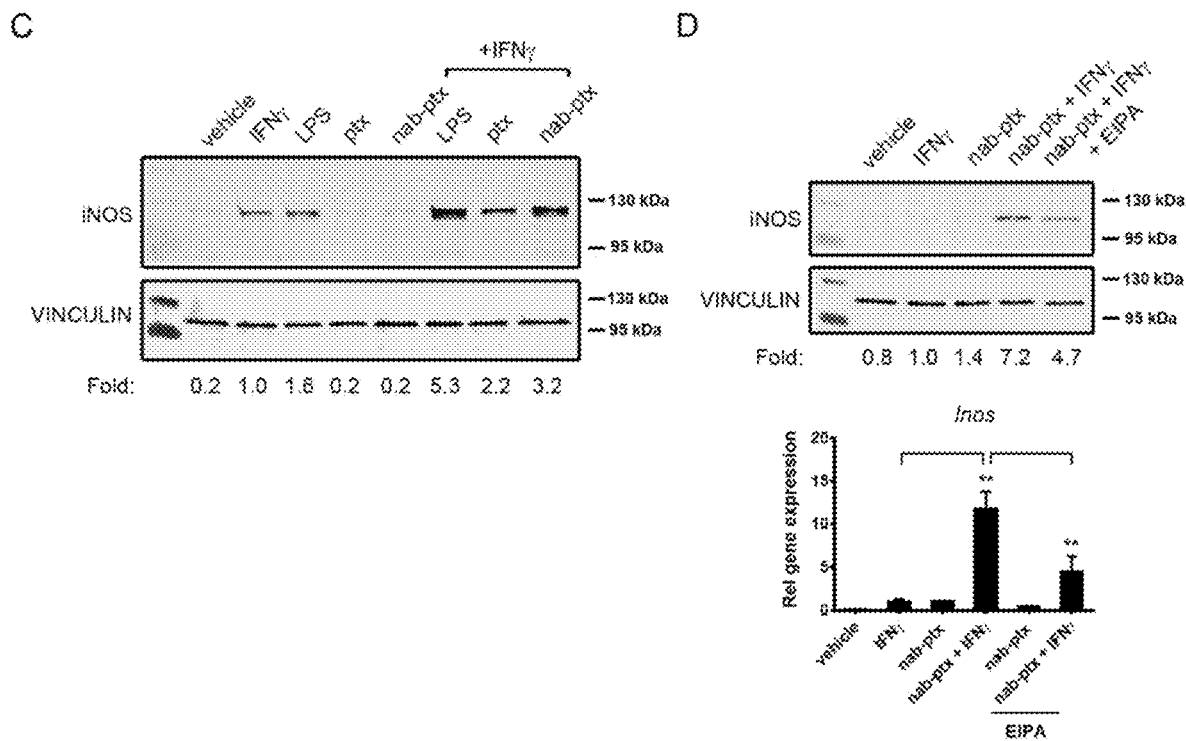
Figure 3A:
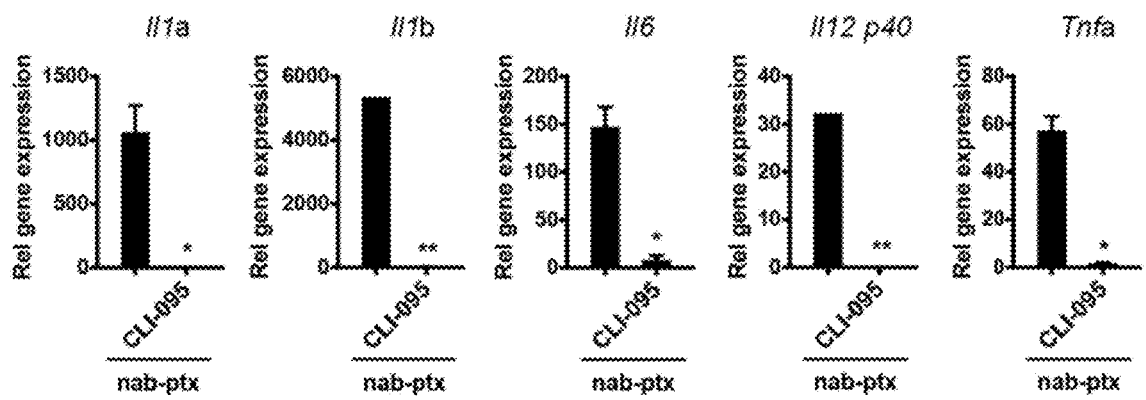
FIGS. 3A-3B show nab-paclitaxel induces M1 activation in a TLR4-dependent manner.
Figure 3B:
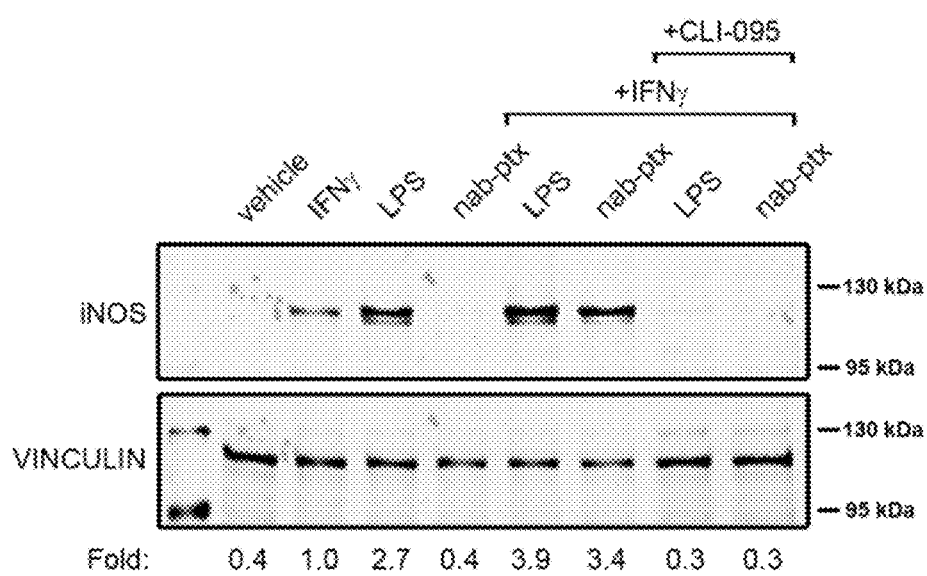
Figure 5:
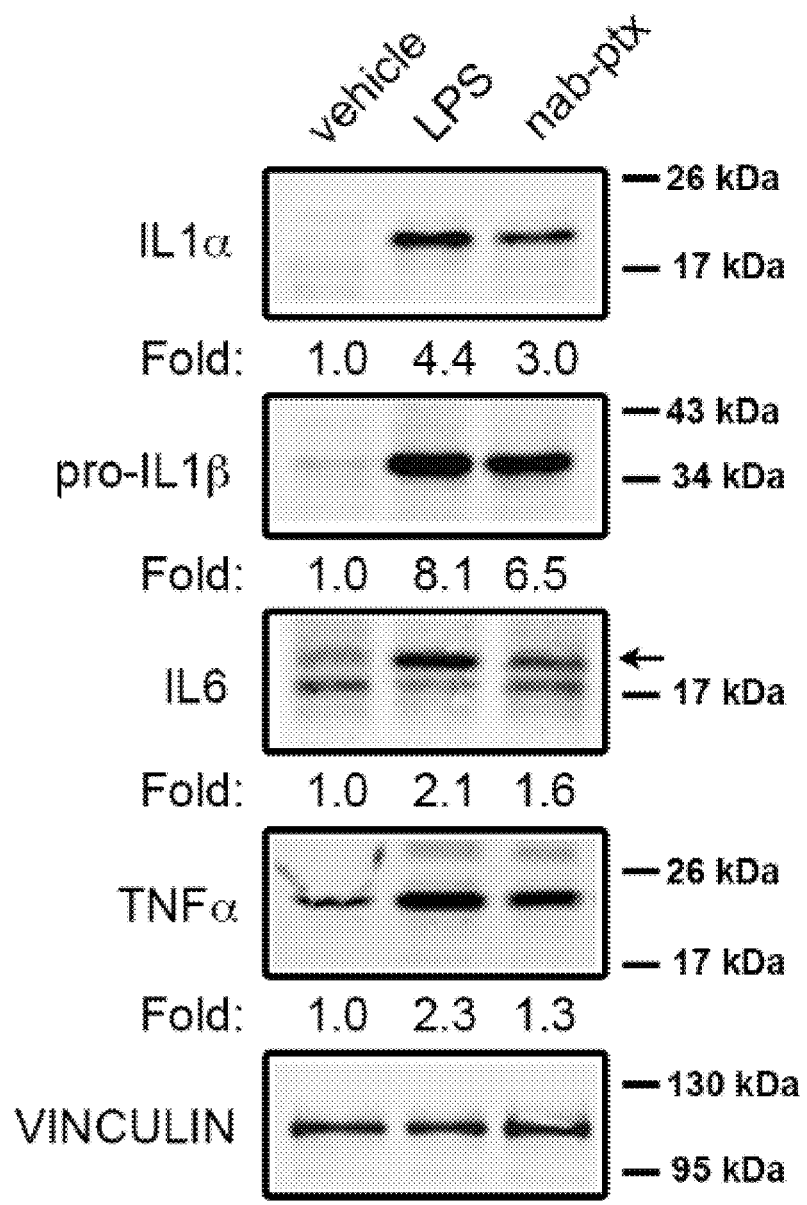
FIG. 5 shows nab-paclitaxel induces M1 cytokine protein expression in vitro. Western blot analysis of IL1α, IL10, IL6 and TNFα expression in RAW 264.7 cells treated with vehicle (PBS), LPS or nab-ptx for 8 hours. VINCULIN served as a protein loading control. Numbers below Western blots indicate level of cytokine induction normalized to VINCULIN and relative to vehicle control.
Figure 6:
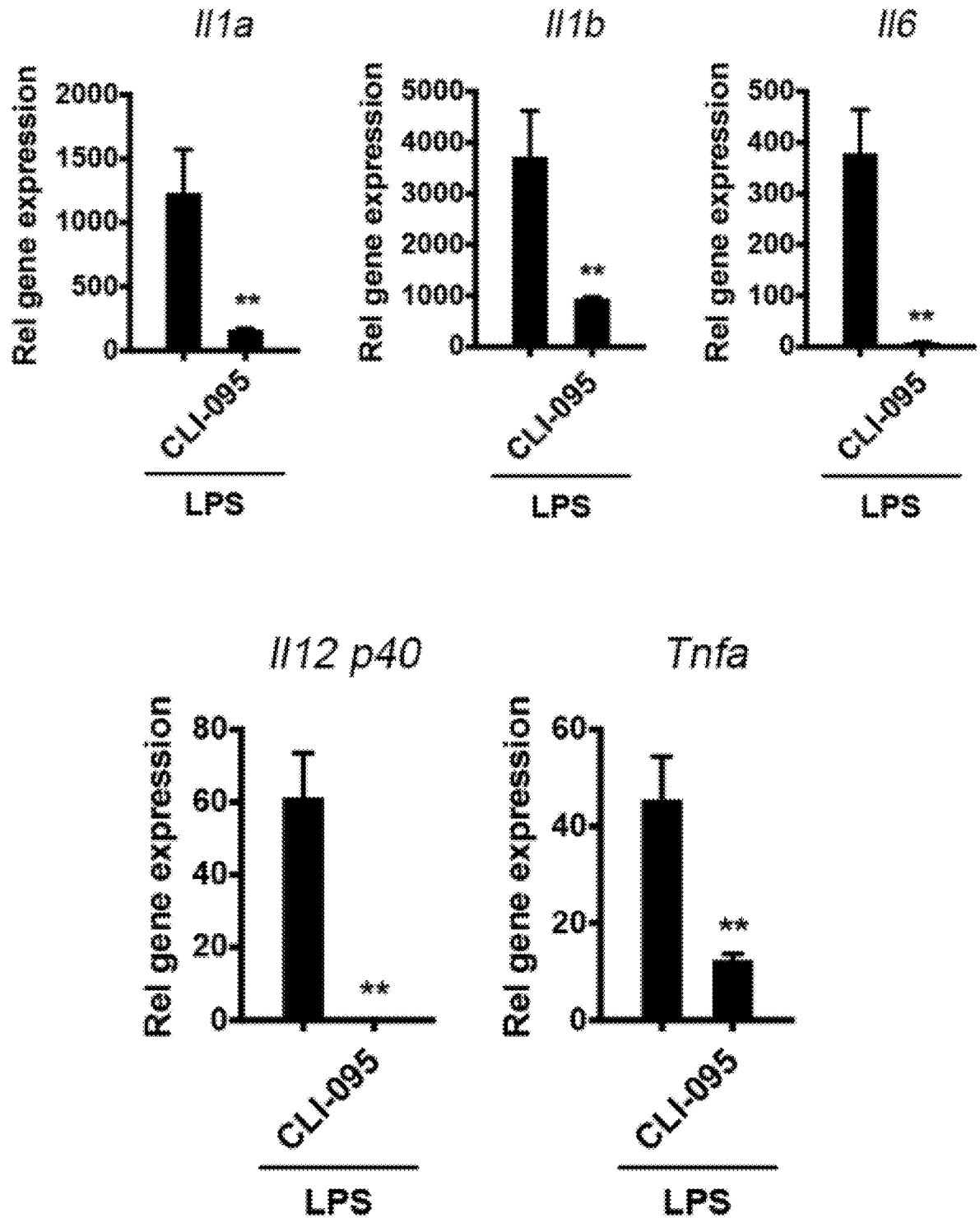
FIG. 6 shows LPS induces M1 cytokine expression in a TLR4-dependent manner. Relative gene expression levels of Il1α, Il1β, Il6, Il12 p40 and Tnfα treated with LPS or with LPS and 5 μM CLI-095. Bars represent standard error from three independent experiments. *, p<0.05; **, p<0.01; ns, not significant.

Consistent with recent findings by Tanei and colleagues (Tanei et al., "Redirecting Transport of Nanoparticle Albumin-Bound Paclitaxel to Macrophages Enhances Therapeutic Efficacy against Liver Metastases," *Cancer Res.* 76:429-39 (2016), which is hereby incorporated by reference in its entirety), significant cytotoxic effects of nab-paclitaxel on macrophages was not observed at concentrations required for its internalization. Therefore, the capacity of nab-paclitaxel to induce macrophage type-1 (M1) activation was assessed. Because paclitaxel promotes M1 polarization by acting as an LPS mimetic (Zimmer et al., "Paclitaxel Binding to Human and Murine MD-2," *J. Biol. Chem.* 283: 27916-26 (2008), which is hereby incorporated by reference in its entirety), the effect of nab-paclitaxel treatment on the induction of a panel of LPS-inducible cytokines was evaluated. Treatment of RAW 264.7 cells with nab-paclitaxel was sufficient to induce the gene expression of Il1α, Il1β, Il6, Il12b (Il12 p40), and Tnfα in a similar manner to free paclitaxel (FIG. 2A). Nab-paclitaxel also increased IL1α, IL13, IL6, and TNFα protein expression to a similar extent as LPS (FIG. 5). Nab-paclitaxel-dependent M1 cytokine expression was inhibited by EIPA and BAPTA-AM, but not by blocking antibodies to the Fc I and III receptors, demonstrating that macropinocytosis was required for its LPS mimetic effects (FIG. 2B). The tumor cell inhibitory function of M1 macrophages is partially attributed to the upregulation of inducible nitric oxide synthase (iNOS), an enzyme that catalyzes the production of tumor cell cytotoxic nitric oxide from L-Arginine (Stuehr et al., "Nitric Oxide. A Macrophage Product Responsible for Cytostasis and Respiratory Inhibition in Tumor Target Cells," *J. Exp. Med.* 169:1543-55 (1989), which is hereby incorporated by reference in its entirety). It has been shown that LPS synergizes with IFNγ to induce iNOS protein expression in macrophages (Lorsbach et al., "Expression of the Nitric Oxide Synthase Gene in Mouse Macrophages Activated for Tumor Cell Killing. Molecular Basis for the Synergy Between Interferon-gamma and Lipopolysaccharide," *J. Biol. Chem.* 268:1908-13 (1993); Manthey et al., "Taxol Provides a Second Signal for Murine Macrophage Tumoricidal Activity," *J. Immunol.* 152:825-31 (1994), which are hereby incorporated by reference in their entirety). Similarly, nab-paclitaxel treatment induced robust iNOS expression in the presence of IFNγ (FIG. 2C). Nab-paclitaxel-driven iNOS gene and protein expression was partially inhibited by EIPA (FIG. 2D), further supporting the idea that macropinocytosis of nab-paclitaxel contributes to its M1 polarizing effects. Paclitaxel induces macrophage activation via binding to myeloid differentiation factor 2 (MD2), an adaptor protein to TLR4 (Zimmer et al., "Paclitaxel Binding to Human and Murine MD-2," *J. Biol. Chem.* 283:27916-26 (2008), which is hereby incorporated by reference in its entirety). Indeed, it was found that the TLR4 inhibitor CLI-095 abrogated nab-paclitaxel and LPS-dependent Il1α, Il1β, Il6, Il12b, and Tnfα gene expression (FIG. 3A and FIG. 6) and iNOS protein expression (FIG. 3B). These results indicate that nab-paclitaxel signals through the TLR4 receptor.

Figures 4A, 4B, 4C:
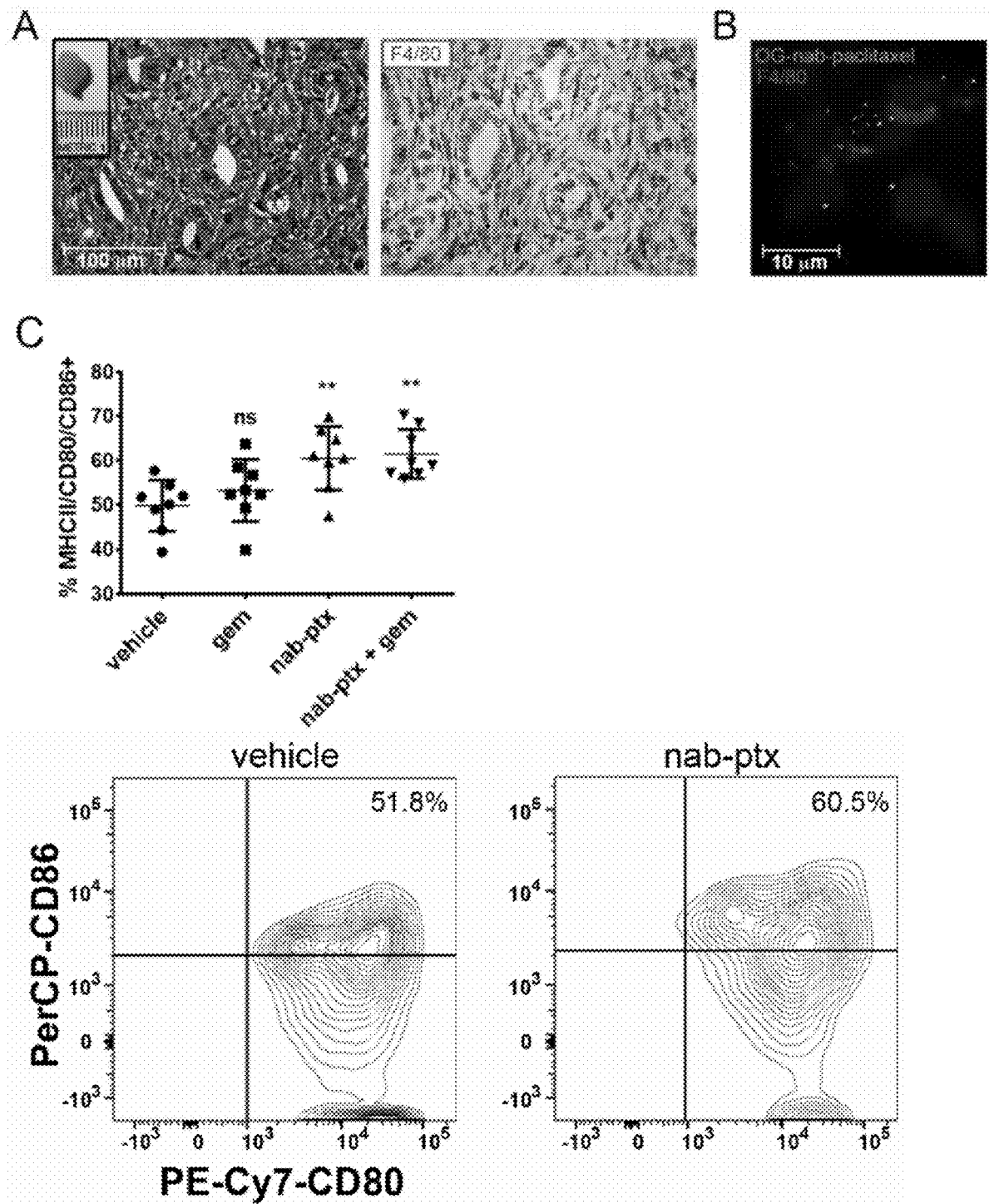
FIGS. 4A-4D show nab-paclitaxel induces M1 activation in pancreatic tumor-associated macrophages in vivo.
Figure 4D:
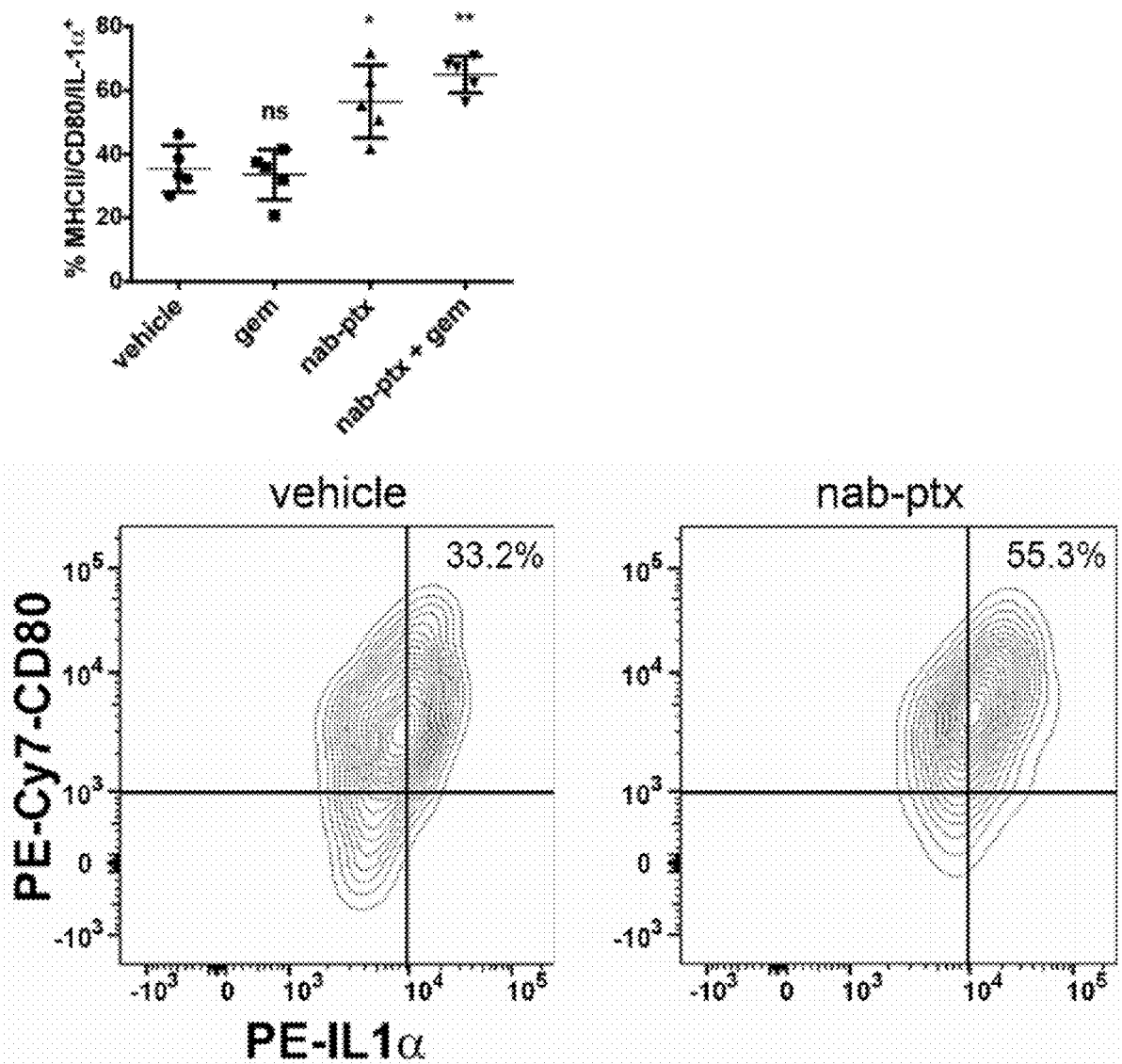
Figures 7A, 7B, 7C:
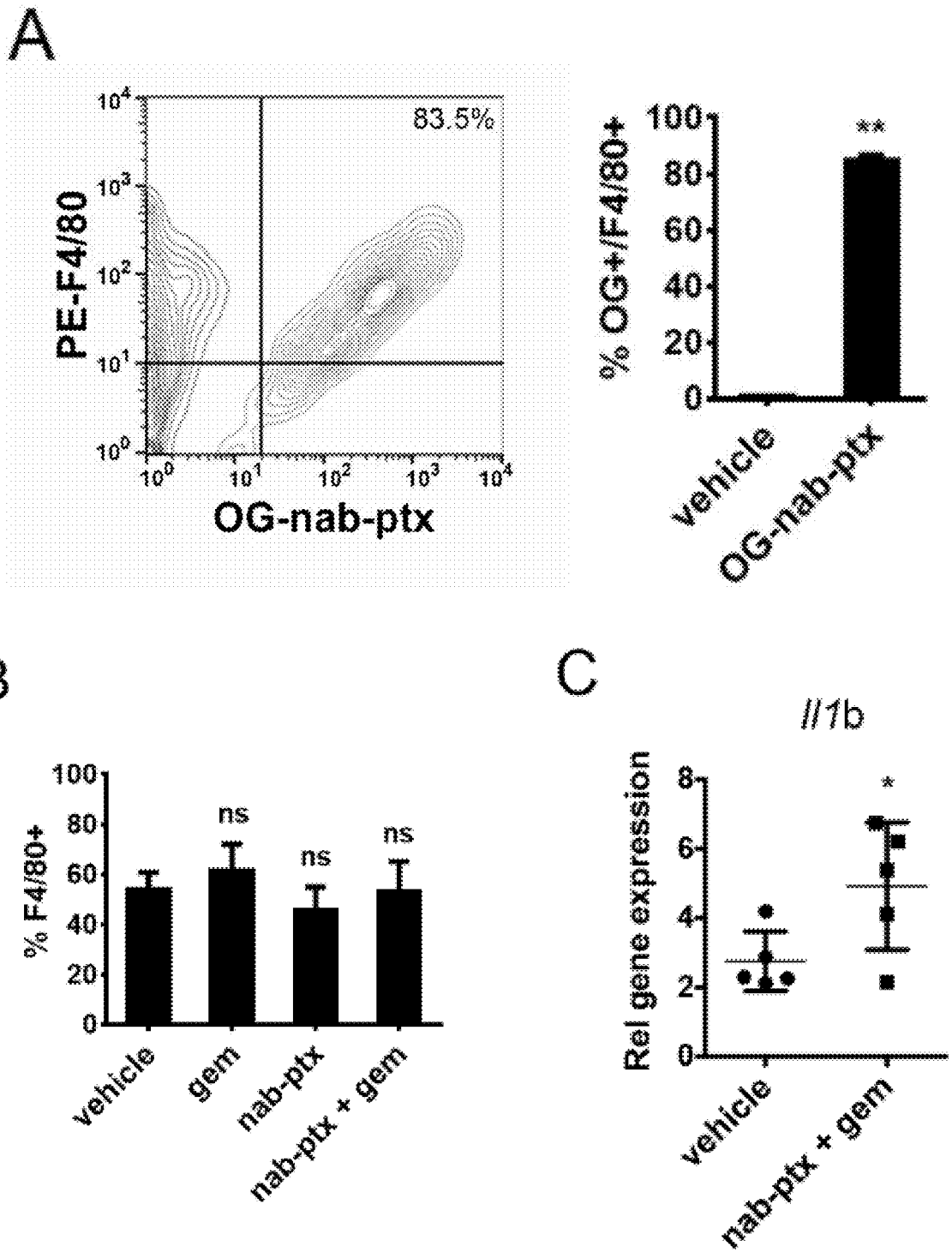
FIGS. 7A-7C shows nab-paclitaxel induces M1 activation in pancreatic tumor-associated macrophages in vivo.

Example 3—Nab-Paclitaxel Induces Type-1 Macrophage Activation in Pancreatic Tumor-Associated Macrophages In Vivo Next, whether nab-paclitaxel could induce M1 polarization of macrophages in the pancreatic tumor microenvironment was determined. To this end, an orthotopic model of PDAC was employed in which cells isolated from primary pancreas tumors of Kras$^{LSL-G12D/+}$, Trp53$^{LSL-R\ 172H/+}$, Pdx1-Cre (KPC) transgenic mice were surgically implanted into the pancreas of immunocompetent syngeneic wild-type animals. In this model, the cells formed tumors within 2 weeks after implantation and exhibited an extensive F4/80$^+$ macrophage infiltrate (FIG. 4A). To determine whether TAMs can internalize nab-paclitaxel, pancreatic tumors were incubated with OG-nab-paclitaxel and found that F4/80$^+$ cells within the tumor took up nab-paclitaxel (FIG. 4B). Moreover, 83% of CD45$^+$/F4/80$^+$ cells isolated from KPC orthotopic tumors by FACS internalized OG-nab-paclitaxel following ex vivo treatment (FIG. 7A). To determine whether nab-paclitaxel internalization induces M1 polarization of pancreatic tumor-associated macrophages in vivo, orthotopic tumor-bearing mice were treated with a single therapeutic dose of nab-paclitaxel, alone or in combination with gemcitabine, and analyzed for the functional activation of macrophages within the tumor 48 hours after treatment (FIG. 4C). Optimal macrophage activation by immunogenic stimuli requires both the upregulation of antigen-presenting MHCII molecules and the induction of T-cell costimulatory molecules CD80 and CD86 at the cell surface (Subauste et al., "Role of CD80 (B7.1) and CD86 (B7.2) in the Immune Response to an Intracellular Pathogen," *J. Immunol.* 160: 1831-40 (1998), which is hereby incorporated by reference in its entirety). Analysis of the MHCII$^+$CD80$^+$CD86$^+$ cell population by flow cytometry revealed that single-agent nab-paclitaxel was sufficient to increase the MHCII$^+$CD80$^+$ CD86$^+$ macrophage population within the tumors compared with vehicle-treated mice, with no change in total macrophage numbers across treatment cohorts (FIG. 4C and FIG. 7B). Nab-paclitaxel treatment also induced an increase in IL1a protein expression in the tumor-associated M1 population compared with vehicle-treated mice (FIG. 4D). Gene expression analysis of the total macrophage population also revealed a 2-fold increase in Il10 expression following treatment with nab-paclitaxel and gemcitabine (FIG. 7C). Together, these data demonstrate that internalization of nab-paclitaxel by pancreatic tumor-associated macrophages can drive them toward an M1 activation state in vivo.

Discussion of Examples 1-3

Taxanes, and in particular paclitaxel, represent an important class of antitumor agents that have proven to be effective in the treatment of a number of solid malignancies. The albumin-bound form of paclitaxel, nab-paclitaxel, has fewer side effects, shows increased tumor cell cytotoxicity, and patients have higher overall response rates, compared with equal doses of solvent-based paclitaxel in breast, non-small cell lung (NSCLC), and pancreatic cancers (Kundrandra and Niu, "Albumin-bound Paclitaxel in Solid Tumors: Clinical Development and Future Directions," *Drug Des Devel Ther* 9:3767-77 (2015), which is hereby incorporated by reference in its entirety). The improved tumor response to nab-paclitaxel has been attributed to elevated intratumoral concentrations mediated by binding of albumin to endothelial 60-kDa glycoprotein receptor (gp60; Desai et al., "Increased Antitumor Activity, Intratumor Paclitaxel Concentrations, and Endothelial Cell Transport of Cremophor-free, Albumin-bound Paclitaxel, ABI-007, Compared With Cremophor-based Paclitaxel," *Clin Cancer Res* 12: 1317-24 (2006), which is hereby incorporated by reference in its entirety.), thereby facilitating vascular transcytosis. It has been proposed that the antitumor activity of nab-paclitaxel might be attributed to its binding to SPARC, a cell surface receptor with sequence homology to gp60 that is expressed on multiple tumor cell types (Desai et al., "Improved Effectiveness of Nanoparticle Albumin-bound (nab) Paclitaxel Versus Polysorbate-based Docetaxel in Multiple Xenografts as a Function of HER2 and SPARC Status," *Anticancer Drugs* 19:899-909 (2008); Desai et al., "SPARC Expression Correlates With Tumor Response to Albumin-bound Paclitaxel in Head and Neck Cancer Patients," *Transl Oncol* 2:59-64 (2009), which are hereby incorporated by reference in their entirety). The findings reported herein suggest that nab-paclitaxel-dependent tumor cell killing may be additionally mediated via its immunostimulatory effects on TAMs. The potential relevance of this tumor cell-extrinsic mechanism in the context of PDAC is supported by the observation that paclitaxel provides limited clinical benefit despite exhibiting comparable effects on microtubule function to nab-paclitaxel in tumor cells (Awasthi et al., "Comparative Benefits of Nab-paclitaxel Over Gemcitabine or Polysorbate-based Docetaxel in Experimental Pancreatic Cancer," *Carcinogenesis* 34:2361-9 (2013), which is hereby incorporated by reference in its entirety). In murine and human studies of PDAC, nab-paclitaxel more effectively reduces stromal density relative to solvent-based taxanes (Awasthi et al., "Comparative Benefits of Nab-paclitaxel over Gemcitabine or Polysorbate-based Docetaxel in Experimental Pancreatic Cancer," *Carcinogenesis* 34:2361-9 (2013); Alvarez et al., "Stromal Disrupting Effects of Nab-paclitaxel in Pancreatic Cancer," *BrJ Cancer* 109:926-33 (2013); Von Hoff et al., "Gemcitabine Plus Nab-paclitaxel is an Active Regimen in Patients With Advanced Pancreatic Cancer: a Phase I/II Trial," *J Clin Oncol* 29:4548-54 (2011); DeNardo et al., "CD4(+) T Cells Regulate Pulmonary Metastasis of Mammary Carcinomas by Enhancing Protumor Properties of Macrophages," *Cancer Cell* 16:91-102 (2009), which are hereby incorporated by reference in their entirety). As the activation of pancreatic stellate cells is influenced by M2 macrophages (Neesse et al., "SPARC Independent Drug Delivery and Antitumour Effects of Nab-paclitaxel in Genetically Engineered Mice," *Gut* 63:974-83 (2014), which is hereby incorporated by reference in its entirety), the stromal-depleting consequences of nab-paclitaxel treatment on the tumor stroma could reflect its effect on macrophage M1 polarization. Both breast cancer and NSCLC, malignancies for which nab-paclitaxel is a standard treatment regimen (Kundranda and Niu, "Albumin-bound Paclitaxel in Solid Tumors: Clinical Development and Future Directions," *Drug Des Devel Ther* 9:3767-77 (2015), which is hereby incorporated by reference in its entirety), have extensive immunosuppressive macrophage infiltrates (Shi et al., "Fibrogenesis in Pancreatic Cancer is a Dynamic Process Regulated by Macrophage-Stellate Cell Interaction," *Lab Invest* 94:409-21 (2014); Tang, "Tumor-associated Macrophages as Potential Diagnostic and Prognostic Biomarkers in Breast Cancer," *Cancer Lett* 332:3-10 (2013), which are hereby incorporated by reference in their entirety). Thus, the proposed mode of action of nab-paclitaxel in promoting macrophage activation might be of broad relevance to tumor sites in which the drug shows therapeutic benefits.

Paclitaxel promotes M1 polarization via direct binding to MD2, an extracellular adaptor protein of TLR4 (Zimmer et al., "Paclitaxel Binding to Human and Murine MD-2," *J Biol Chem* 283:27916-26 (2008), which is hereby incorporated by reference in its entirety). Upon activation, TLR4 is rapidly internalized into endosomes and engages downstream signaling pathways via endocytic shuttling (Ma et al., "The M1 Form of Tumor-associated Macrophages in Non-small Cell Lung Cancer is Positively Associated With Survival Time," *BMC Cancer* 10:112 (2010), which is hereby incorporated by reference in its entirety). TLR4 internalization and trafficking is required for efficient LPS-dependent TLR4 signal propagation (Ma et al., "The M1 Form of Tumor-associated Macrophages in Non-small Cell Lung Cancer is Positively Associated With Survival Time," *BMC Cancer* 10:112 (2010), which is hereby incorporated by reference in its entirety). Although macropinosomes and endosomes are formed as distinct vesicular entities, they fuse in the course of their intracellular trafficking (Latz et al., "Lipopolysaccharide Rapidly Traffics to and From the Golgi Apparatus With the Toll-like Receptor 4-MD-2-CD14 Complex in a Process That is Distinct From the Initiation of Signal transduction," *J Blot Chem* 277:47834-43 (2002), which is hereby incorporated by reference in its entirety). It is therefore plausible that the macropinocytic uptake of nab-paclitaxel enables it to act on endosomal TLR4 complexes. Whether this mode of activation provides the means to increase the local effective concentration of paclitaxel, and/or induce a different signaling repertoire, remains to be established. Inflammatory stimuli, including IFNγ and TNFα, induce a shift from phagocytosis to macropinocytosis for the internalization of pathogens by macrophages (Racoosin and Swanson, "Macropinosome Maturation and Fusion With Tubular Lysosomes in Macrophages," *J Cell Biol* 121:1011-20 (1993), which is hereby incorporated by reference in its entirety). Nab-paclitaxel-mediated M1 induction may therefore result in positive feedback signaling, promoting further uptake of drug and enhancing its M1-activating effects in both an autocrine and paracrine fashion. Together, these data support the hypothesis that macropinocytosis of the albumin formulation of paclitaxel promotes its M1-polarizing effects and may account for its elevated activity over solvent-based formulations of paclitaxel. One study suggests that nab-paclitaxel treatment may induce tumor cell toxicity via its internalization and subsequent release by macrophages in the tumor microenvironment (Tanei et al., "Redirecting Transport of Nanoparticle Albumin-bound Paclitaxel to Macrophages Enhances Therapeutic Efficacy Against Liver Metastases," *Cancer Res* 76:429-39 (2016), which is hereby incorporated by reference in its entirety). However, because a direct uptake of nab-paclitaxel by macrophages was not formally demonstrated in that study, the relevance of this proposed mechanism to our findings that nab-paclitaxel mediates M1 activation cannot be ascertained.

Single-agent immunotherapies designed to activate cytotoxic T cells have shown little benefit in PDAC, despite showing efficacy in many solid tumors (Bosedasgupta and Pieters, "Inflammatory Stimuli Reprogram Macrophage Phagocytosis to Macropinocytosis for the Rapid Elimination of Pathogens," *PLoS Pathog* 10: e1003879 (2014); Brahmer et al., "Safety and Activity of Anti-PD-L1 Antibody in Patients With Advanced Cancer," *N Engl J Med* 366:2455-65 (2012); Le et al., "Evaluation of Ipilimumab in Combination With Allogeneic Pancreatic Tumor Cells Transfected With a GM-CSF Gene in Previously Treated Pancreatic Cancer," *J Immunother* 36:382-9 (2013), which are hereby incorporated by reference in their entirety). Given that pancreatic tumor-associated macrophages can contribute to an immunosuppressive microenvironment by inhibiting cytotoxic T-cell function (Royal et al., "Phase 2 Trial of Single Agent Ipilimumab (anti-CTLA-4) for Locally Advanced or Metastatic Pancreatic Adenocarcinoma," *J Immunother* 33:828-33 (2010), which is hereby incorporated by reference in its entirety), immune recognition may be improved by combining nab-paclitaxel with T-cell immunotherapies. Considering the highly immunocompromised microenvironment of PDAC, however, it is likely that more potent M1 agonists may be required to restore immune surveillance. Several macrophage-activating immunotherapies are in clinical trials for the treatment of a variety of malignancies, including blocking antibodies to colony stimulating factor 1 (De Palma and Lewis, "Macrophage regulation of tumor responses to anticancer therapies," *Cancer Cell* 23:277-86 (2013), which is hereby incorporated by reference in its entirety); TLR-activating agents PAM3CSK4 (Pyonteck et al., "CSF-1R Inhibition Alters Macrophage Polarization and Blocks Glioma Progression,"

Nat Med 19:1264-72 (2013), which is hereby incorporated by reference in its entirety) and Poly I:C (Vogelpoel et al., "Fc gamma Receptor-TLR Cross-talk Elicits Pro-inflammatory Cytokine Production by Human M2 Macrophages," Nat Commun 5:5444 (2014), which is hereby incorporated by reference in its entirety); and blocking antibodies to IL10 (Cui et al., "Identification and Characterization of Poly(I:C)-induced Molecular Responses Attenuated by Nicotine in Mouse Macrophages," Mol Pharmacol 83:61-72 (2013), which is hereby incorporated by reference in its entirety). It is possible that coupling such agents to albumin nanoparticles, in particular, modified albumin nanoparticles having reduced or defective FcRN binding affinity, may improve their delivery to macrophages in the tumor microenvironment and more efficiently restore immune recognition. Employing albumin nanoparticles, in particular modified albumin nanoparticles having reduced or defective FcRN binding affinity, as vehicles for macrophage-activating agents may therefore serve broad applicability in a variety of tumor types exhibiting extensive M2 infiltration.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of treating a tumor in a subject comprising: selecting a subject having a tumor and administering to the selected subject an anti-tumor agent coupled to a carrier molecule selected from (i) a modified or variant human albumin protein or fragment thereof, and (ii) a modified or variant human immunoglobulin G protein or fragment thereof, wherein the carrier molecule is defective in neonatal Fc receptor (FcRn) binding, wherein said anti-tumor agent and carrier molecule are taken up via macropinocytosis by monocytes and/or macrophages within the tumor microenvironment, thereby activating the monocytes and/or macrophages to have an anti-tumor immune response.

2. The method of claim 1, wherein the tumor is characterized by tumor cells expressing FcRn.

3. The method of claim 1, wherein the anti-tumor agent is a chemotherapeutic agent.

4. The method of claim 1, wherein the chemotherapeutic agent is a taxane.

5. The method of claim 3, wherein the taxane is paclitaxel.

6. The method of claim 1, wherein the carrier molecule is a modified or variant human albumin protein or fragment thereof.

7. The method of claim 6, wherein the modified or variant human albumin protein or fragment thereof comprises one or more amino acid modifications at one or more amino acid positions corresponding to 464, 494, 495, 496, 499, 500, 510, 535, 536, 537, 538, and 573 of SEQ ID NO: 1.

8. The method of claim 7, wherein the modified or variant human albumin protein or fragment thereof comprises one or more amino acid modifications selected from the group consisting of D494N, D494Q, D494A, E495Q, E495A, T496A, P499A, K536A, P537A, K538A, K500A, K573STOP, H464Q, H510Q, and H535Q.

9. The method of claim 1, wherein the anti-tumor agent is paclitaxel and the carrier molecule is a modified or variant human albumin protein or fragment thereof.

10. The method of claim 1, wherein the carrier molecule defective in FcRn binding is a modified or variant immunoglobulin G protein or fragment thereof.

11. A method of treating a tumor in a subject comprising: selecting a subject having a tumor characterized by tumor cells expressing FcRn; and administering to the selected subject an anti-tumor agent coupled to a carrier molecule selected from (i) a modified or variant human albumin protein or fragment thereof and (ii) a modified or variant human immunoglobulin G protein or fragment thereof, wherein the carrier molecule is defective in neonatal Fc receptor (FcRn) binding, wherein said anti-tumor agent and carrier molecule are taken up by the tumor cells expressing FcRn to cause tumor cell death.

12. The method of claim 11, wherein the anti-tumor agent is a chemotherapeutic agent.

13. The method of claim 12, wherein the chemotherapeutic agent is a taxane.

14. The method of claim 13, wherein the taxane is paclitaxel.

15. The method of claim 11, wherein the carrier molecule is a modified or variant human albumin protein or fragment thereof.

16. The method of claim 15, wherein the modified or variant human albumin protein or fragment thereof comprises one or more amino acid modifications at one or more amino acid positions corresponding to 464, 494, 495, 496, 499, 500, 510, 535, 536, 537, 538, and 573 of SEQ ID NO: 1.

17. The method of claim 16, wherein the modified or variant human albumin protein or fragment thereof comprises one or more amino acid modifications selected from the group consisting of D494N, D494Q, D494A, E495Q, E495A, T496A, P499A, K536A, P537A, K538A, K500A, K573STOP, H464Q, H510Q, and H535Q.

18. The method of claim 11, wherein the anti-tumor agent is paclitaxel and the carrier molecule is a modified or variant human albumin protein or fragment thereof.

19. The method of claim 11, wherein the carrier molecule defective in FcRn binding is a modified or variant immunoglobulin G protein or fragment thereof.

* * * * *

UNITED STATES PATENT AND TRADEMARK OFFICE
CERTIFICATE OF CORRECTION

PATENT NO. : 12,016,881 B2  
APPLICATION NO. : 17/396792  
DATED : June 25, 2024  
INVENTOR(S) : Bar-Sagi et al.

Page 1 of 1

It is certified that error appears in the above-identified patent and that said Letters Patent is hereby corrected as shown below:

In the Specification

At Column 1, at Line 17 (before the section heading "FIELD OF THE INVENTION"), insert the following new paragraph:
--This invention was made with government support under AI100853, CA009161, and HL007151 awarded by the National Institutes of Health. The government has certain rights in the invention.--

Signed and Sealed this  
Twenty-eighth Day of October, 2025

John A. Squires  
*Director of the United States Patent and Trademark Office*

SEQUENCE LISTING

<160> NUMBER OF SEQ ID NOS: 17

<210> SEQ ID NO 1
<211> LENGTH: 585
<212> TYPE: PRT
<213> ORGANISM: Homo sapiens

<400> SEQUENCE: 1

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270
```

```
Ser Lys Leu Lys Glu Cys Cys Glu Lys Pro Leu Leu Glu Lys Ser His
            275                 280                 285
Cys Ile Ala Glu Val Glu Asn Asp Glu Met Pro Ala Asp Leu Pro Ser
        290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Arg Leu Ala Lys Thr
                340                 345                 350
Tyr Glu Thr Thr Leu Glu Lys Cys Cys Ala Ala Ala Asp Pro His Glu
            355                 360                 365
Cys Tyr Ala Lys Val Phe Asp Glu Phe Lys Pro Leu Val Glu Glu Pro
        370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Leu His
            450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
        515                 520                 525
Leu Val Glu Leu Val Lys His Lys Pro Lys Ala Thr Lys Glu Gln Leu
            530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu
            580                 585

<210> SEQ ID NO 2
<211> LENGTH: 21
<212> TYPE: DNA
<213> ORGANISM: Artificial
<220> FEATURE:
<223> OTHER INFORMATION: Primer

<400> SEQUENCE: 2
aatcaagatg gccaaagttc c                                         21

<210> SEQ ID NO 3
<211> LENGTH: 23
<212> TYPE: DNA
<213> ORGANISM: Artificial
<220> FEATURE:
<223> OTHER INFORMATION: Primer
```

<400> SEQUENCE: 3
attcagagag agatggtcaa tgg                                              23

<210> SEQ ID NO 4
<211> LENGTH: 22
<212> TYPE: DNA
<213> ORGANISM: Artificial
<220> FEATURE:
<223> OTHER INFORMATION: Primer

<400> SEQUENCE: 4
gcaactgttc ctgaactcaa ct                                               22

<210> SEQ ID NO 5
<211> LENGTH: 21
<212> TYPE: DNA
<213> ORGANISM: Artificial
<220> FEATURE:
<223> OTHER INFORMATION: Primer

<400> SEQUENCE: 5
atcttttggg gtccgtcaac t                                                21

<210> SEQ ID NO 6
<211> LENGTH: 23
<212> TYPE: DNA
<213> ORGANISM: Artificial
<220> FEATURE:
<223> OTHER INFORMATION: Primer

<400> SEQUENCE: 6
tagtccttcc taccccaatt tcc                                              23

<210> SEQ ID NO 7
<211> LENGTH: 21
<212> TYPE: DNA
<213> ORGANISM: Artificial
<220> FEATURE:
<223> OTHER INFORMATION: Primer

<400> SEQUENCE: 7
ttggtcctta gccactcctt c                                                21

<210> SEQ ID NO 8
<211> LENGTH: 23
<212> TYPE: DNA
<213> ORGANISM: Artificial
<220> FEATURE:
<223> OTHER INFORMATION: Primer

<400> SEQUENCE: 8
gttctcagcc caacaataca aga                                              23

<210> SEQ ID NO 9
<211> LENGTH: 19
<212> TYPE: DNA
<213> ORGANISM: Artificial
<220> FEATURE:
<223> OTHER INFORMATION: Primer

<400> SEQUENCE: 9
gtggacgggt cgatctcac                                                   19

<210> SEQ ID NO 10

```
<211> LENGTH: 19
<212> TYPE: DNA
<213> ORGANISM: Artificial
<220> FEATURE:
<223> OTHER INFORMATION: Primer

<400> SEQUENCE: 10
ctgtagccca cgtcgtagc                                                19

<210> SEQ ID NO 11
<211> LENGTH: 18
<212> TYPE: DNA
<213> ORGANISM: Artificial
<220> FEATURE:
<223> OTHER INFORMATION: Primer

<400> SEQUENCE: 11
ttgagatcca tgccgttg                                                 18

<210> SEQ ID NO 12
<211> LENGTH: 21
<212> TYPE: DNA
<213> ORGANISM: Artificial
<220> FEATURE:
<223> OTHER INFORMATION: Primer

<400> SEQUENCE: 12
tggtttgcca tcgttttgct g                                             21

<210> SEQ ID NO 13
<211> LENGTH: 22
<212> TYPE: DNA
<213> ORGANISM: Artificial
<220> FEATURE:
<223> OTHER INFORMATION: Primer

<400> SEQUENCE: 13
acaggtgagg ttcactgttt ct                                            22

<210> SEQ ID NO 14
<211> LENGTH: 24
<212> TYPE: DNA
<213> ORGANISM: Artificial
<220> FEATURE:
<223> OTHER INFORMATION: Primer

<400> SEQUENCE: 14
cacggcaaat tcaacggcac agtc                                          24

<210> SEQ ID NO 15
<211> LENGTH: 22
<212> TYPE: DNA
<213> ORGANISM: Artificial
<220> FEATURE:
<223> OTHER INFORMATION: Primer

<400> SEQUENCE: 15
acccgtttgg ctccaccctt ca                                            22

<210> SEQ ID NO 16
<211> LENGTH: 20
<212> TYPE: DNA
<213> ORGANISM: Artificial
<220> FEATURE:
<223> OTHER INFORMATION: Primer

<400> SEQUENCE: 16
```

```
gtctgatccg caaatacggg                                            20

<210> SEQ ID NO 17
<211> LENGTH: 21
<212> TYPE: DNA
<213> ORGANISM: Artificial
<220> FEATURE:
<223> OTHER INFORMATION: Primer

<400> SEQUENCE: 17
agcctatgtc cttcgcgtac t                                          21
```